(12) United States Patent
Rodriguez-Navarro et al.

(10) Patent No.: US 12,262,971 B2
(45) Date of Patent: Apr. 1, 2025

(54) ONE-OPERATOR SURGICAL SYSTEM AND METHODS OF USE

(71) Applicant: Levita Magnetics International Corp., San Mateo, CA (US)

(72) Inventors: Alberto Rodriguez-Navarro, San Francisco, CA (US); Bryan Loomas, Los Gatos, CA (US)

(73) Assignee: LEVITA MAGNETICS INTERNATIONAL CORP., Mountain View, CA (US)

( * ) Notice: Subject to any disclaimer, the term of this patent is extended or adjusted under 35 U.S.C. 154(b) by 503 days.

(21) Appl. No.: 16/008,976

(22) Filed: Jun. 14, 2018

(65) Prior Publication Data

US 2018/0296289 A1    Oct. 18, 2018

Related U.S. Application Data

(63) Continuation of application No. PCT/US2017/012628, filed on Jan. 6, 2017.
(Continued)

(51) Int. Cl.
*A61B 34/00* (2016.01)
*A61B 1/00* (2006.01)
(Continued)

(52) U.S. Cl.
CPC .......... *A61B 34/73* (2016.02); *A61B 1/00042* (2022.02); *A61B 1/00045* (2013.01);
(Continued)

(58) Field of Classification Search
CPC ....... A61B 34/73; A61B 90/50; A61B 90/361; A61B 34/25; A61B 34/76; A61B 1/126;
(Continued)

(56) References Cited

U.S. PATENT DOCUMENTS 2,678,228 A    5/1954  Gerhardt
2,863,444 A   12/1958  Winsten
(Continued)

FOREIGN PATENT DOCUMENTS

AU    2016204942 A1 *  2/2017   .......... A61B 5/0035
CA    2 748 471 A1     7/2010
(Continued)

OTHER PUBLICATIONS

Final Office Action mailed on Nov. 25, 2020, for U.S. Appl. No. 15/728,297, filed Oct. 9, 2017, 11 pages.
(Continued)

*Primary Examiner* — Anh Tuan T Nguyen
*Assistant Examiner* — Shankar Raj Ghimire
(74) *Attorney, Agent, or Firm* — Cooley LLP

(57) ABSTRACT

Described here are systems, devices, and methods useful for minimally invasive surgical procedures performed by a single operator. The surgical systems may include a user interface, a display, one or more support arms each comprising an external magnet, and one or more intracavity devices. The intracavity devices may be configured to be attracted to respective external magnets. The user interface may be configured to allow the operator to control the location and orientation of the intracavity devices by control of the position of the support arms and magnetic field of the external magnet.

18 Claims, 19 Drawing Sheets

Related U.S. Application Data

(60) Provisional application No. 62/276,752, filed on Jan. 8, 2016.

(51) Int. Cl.

| | | |
|---|---|---|
| A61B 1/04 | (2006.01) | |
| A61B 1/12 | (2006.01) | |
| A61B 17/00 | (2006.01) | |
| A61B 17/02 | (2006.01) | |
| A61B 17/29 | (2006.01) | |
| A61B 90/00 | (2016.01) | |
| A61B 90/30 | (2016.01) | |
| A61B 90/50 | (2016.01) | |
| A61B 34/20 | (2016.01) | |
| A61B 34/30 | (2016.01) | |

(52) U.S. Cl.
CPC .......... *A61B 1/00158* (2013.01); *A61B 1/041* (2013.01); *A61B 1/126* (2013.01); *A61B 17/0218* (2013.01); *A61B 17/29* (2013.01); *A61B 34/25* (2016.02); *A61B 34/76* (2016.02); *A61B 90/361* (2016.02); *A61B 90/50* (2016.02); *A61B 1/00087* (2013.01); *A61B 2017/00057* (2013.01); *A61B 2017/00075* (2013.01); *A61B 2017/00084* (2013.01); *A61B 2017/00115* (2013.01); *A61B 2017/00119* (2013.01); *A61B 2017/00199* (2013.01); *A61B 2017/00203* (2013.01); *A61B 2017/00207* (2013.01); *A61B 2017/00283* (2013.01); *A61B 2017/00473* (2013.01); *A61B 2017/00477* (2013.01); *A61B 2017/00876* (2013.01); *A61B 2017/2929* (2013.01); *A61B 2017/2947* (2013.01); *A61B 2034/2048* (2016.02); *A61B 34/30* (2016.02); *A61B 90/30* (2016.02); *A61B 2090/508* (2016.02); *A61B 2562/0223* (2013.01); *A61B 2562/0257* (2013.01)

(58) Field of Classification Search
CPC . A61B 17/29; A61B 17/0218; A61B 1/00039; A61B 1/00045; A61B 1/00158; A61B 1/041; A61B 90/30; A61B 34/30; A61B 2017/00199; A61B 1/00087; A61B 2562/0223; A61B 2562/0257; A61B 2017/00876; A61B 5/062; A61B 17/1707
See application file for complete search history.

(56) References Cited

U.S. PATENT DOCUMENTS

| | | |
|---|---|---|
| 3,146,381 A | 8/1964 | Louis |
| 3,674,014 A | 7/1972 | Tillander |
| 3,789,285 A | 1/1974 | Nishizawa |
| 3,794,091 A | 2/1974 | Ersek et al. |
| 4,364,377 A | 12/1982 | Smith |
| 4,380,999 A | 4/1983 | Healy |
| 4,706,668 A | 11/1987 | Backer |
| 4,756,312 A | 7/1988 | Epley |
| 4,901,405 A | 2/1990 | Grover et al. |
| 4,915,435 A | 4/1990 | Levine |
| 4,968,136 A | 11/1990 | Lim et al. |
| 4,971,067 A | 11/1990 | Bolduc et al. |
| 4,976,723 A | 12/1990 | Schad |
| 4,997,436 A | 3/1991 | Oberlander |
| 5,002,557 A | 3/1991 | Hasson |
| 5,154,189 A | 10/1992 | Oberlander |
| 5,156,608 A | 10/1992 | Troidl et al. |
| 5,156,609 A | 10/1992 | Nakao et al. |
| 5,282,806 A | 2/1994 | Haber et al. |
| 5,300,081 A | 4/1994 | Young et al. |
| 5,304,183 A | 4/1994 | Gourlay et al. |
| 5,304,185 A | 4/1994 | Taylor |
| 5,307,805 A | 5/1994 | Byrne |
| 5,340,360 A | 8/1994 | Stefanchik |
| 5,397,325 A | 3/1995 | Della Badia |
| 5,411,535 A | 5/1995 | Fujii et al. |
| 5,415,160 A | 5/1995 | Ortiz et al. |
| 5,417,701 A | 5/1995 | Holmes |
| 5,449,361 A | 9/1995 | Preissman |
| 5,449,365 A | 9/1995 | Green et al. |
| 5,450,842 A | 9/1995 | Tovey et al. |
| 5,458,603 A | 10/1995 | Futch, Sr. |
| 5,458,693 A | 10/1995 | Codorniu |
| 5,465,711 A | 11/1995 | Moll et al. |
| 5,496,317 A | 3/1996 | Goble et al. |
| 5,499,986 A | 3/1996 | Dimarco |
| 5,529,568 A | 6/1996 | Rayman |
| 5,538,098 A | 7/1996 | Sparhawk |
| 5,567,274 A | 10/1996 | Funk et al. |
| 5,569,274 A | 10/1996 | Rapacki et al. |
| 5,593,379 A | 1/1997 | Rayman |
| 5,595,562 A | 1/1997 | Grier |
| 5,654,864 A | 8/1997 | Ritter et al. |
| 5,665,100 A | 9/1997 | Yoon |
| 5,681,260 A | 10/1997 | Ueda et al. |
| 5,728,121 A | 3/1998 | Bimbo et al. |
| 5,733,292 A | 3/1998 | Gustilo et al. |
| 5,749,881 A | 5/1998 | Sackier et al. |
| 5,766,189 A | 6/1998 | Matsuno |
| 5,782,748 A | 7/1998 | Palmer et al. |
| 5,797,911 A | 8/1998 | Sherman et al. |
| 5,797,939 A | 8/1998 | Yoon |
| 5,824,041 A | 10/1998 | Lenker et al. |
| 5,848,969 A | 12/1998 | Panescu et al. |
| 5,849,015 A | 12/1998 | Haywood et al. |
| 5,888,196 A | 3/1999 | Bonutti |
| 5,893,873 A | 4/1999 | Rader et al. |
| 5,933,926 A | 8/1999 | Reiter |
| 6,015,414 A | 1/2000 | Werp et al. |
| 6,017,358 A | 1/2000 | Yoon et al. |
| 6,096,038 A | 8/2000 | Michelson |
| 6,099,537 A | 8/2000 | Sugai et al. |
| 6,099,550 A | 8/2000 | Yoon |
| 6,123,657 A | 9/2000 | Ishikawa et al. |
| 6,126,647 A | 10/2000 | Posey et al. |
| 6,127,757 A | 10/2000 | Swinbanks |
| 6,165,180 A | 12/2000 | Cigaina et al. |
| 6,173,715 B1 | 1/2001 | Sinanan et al. |
| 6,212,419 B1 | 4/2001 | Blume et al. |
| 6,216,028 B1* | 4/2001 | Haynor ............... A61B 5/06 128/899 |
| 6,241,671 B1 | 6/2001 | Ritter et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,340,365 B2 | 1/2002 | Dittrich et al. |
| 6,358,196 B1 | 3/2002 | Rayman |
| 6,371,973 B1 | 4/2002 | Tepper |
| 6,398,791 B1 | 6/2002 | Que et al. |
| 6,399,146 B1 | 6/2002 | Harris et al. |
| 6,401,723 B1 | 6/2002 | Garibaldi et al. |
| 6,440,133 B1 | 8/2002 | Beale et al. |
| 6,458,146 B1 | 10/2002 | Kramer |
| 6,459,924 B1 | 10/2002 | Creighton, IV et al. |
| 6,464,710 B1 | 10/2002 | Foster |
| 6,488,615 B1 | 12/2002 | Mitchiner et al. |
| 6,523,919 B1 | 2/2003 | Israelsen et al. |
| 6,537,196 B1 | 3/2003 | Creighton, IV et al. |
| 6,551,304 B1 | 4/2003 | Whalen et al. |
| 6,594,517 B1 | 7/2003 | Nevo |
| 6,630,879 B1 | 10/2003 | Creighton, IV et al. |
| 6,632,229 B1 | 10/2003 | Yamanouchi |
| 6,641,595 B1 | 11/2003 | Moran et al. |
| 6,656,199 B1 | 12/2003 | Lafontaine |
| 6,677,752 B1 | 1/2004 | Creighton, IV et al. |
| 6,689,119 B1 | 2/2004 | Di Caprio et al. |
| 6,702,804 B1 | 3/2004 | Ritter et al. |
| 6,705,989 B2 | 3/2004 | Cuschieri et al. |
| 6,719,765 B2 | 4/2004 | Bonutti |
| 6,761,681 B2 | 7/2004 | Schmid et al. |

(56) References Cited

U.S. PATENT DOCUMENTS

| | | | |
|---|---|---|---|
| 6,786,219 B2 | 9/2004 | Garibaldi et al. |
| 6,817,364 B2 | 11/2004 | Garibaldi et al. |
| 6,824,511 B1 | 11/2004 | Bell et al. |
| 6,916,314 B2 | 7/2005 | Schneider et al. |
| 7,017,584 B2 | 3/2006 | Garibaldi et al. |
| 7,094,245 B2 | 8/2006 | Adams et al. |
| 7,169,104 B2 | 1/2007 | Ueda et al. |
| 7,182,089 B2 | 2/2007 | Ries |
| 7,182,775 B2 | 2/2007 | De Guillebon et al. |
| 7,189,198 B2 | 3/2007 | Harburn et al. |
| 7,264,584 B2 | 9/2007 | Ritter et al. |
| 7,300,400 B2 | 11/2007 | Brown |
| 7,311,107 B2 | 12/2007 | Harel et al. |
| 7,313,429 B2 | 12/2007 | Creighton, IV et al. |
| 7,314,063 B2 | 1/2008 | Egli |
| 7,341,063 B2 | 3/2008 | Garbibaldi et al. |
| 7,344,553 B2 | 3/2008 | Opolski et al. |
| 7,390,298 B2 | 6/2008 | Chu |
| 7,416,335 B2 | 8/2008 | Munger |
| 7,429,259 B2 | 9/2008 | Cadeddu et al. |
| 7,431,726 B2 | 10/2008 | Spence et al. |
| 7,566,038 B2 | 7/2009 | Scott et al. |
| 7,618,435 B2 | 11/2009 | Opolski |
| 7,686,827 B2 | 3/2010 | Hushka |
| 7,691,103 B2 | 4/2010 | Fernandez et al. |
| 7,691,731 B2 | 4/2010 | Bet et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,942,885 B2 | 5/2011 | Sixto, Jr. et al. |
| 7,963,903 B2 | 6/2011 | Ghiron et al. |
| 7,966,059 B2 | 6/2011 | Creighton, IV et al. |
| 7,967,830 B2 | 6/2011 | Ayala et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,074,657 B2 | 12/2011 | Scott et al. |
| 8,082,035 B2 | 12/2011 | Glukhovsky |
| 8,133,254 B2 | 3/2012 | Dumbauld et al. |
| 8,136,888 B2 | 3/2012 | Suzuki et al. |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,226,690 B2 | 7/2012 | Altarac et al. |
| 8,235,272 B2 | 8/2012 | Nicholas et al. |
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,343,171 B2 | 1/2013 | Farritor et al. |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,403,916 B2 | 3/2013 | Prescott |
| 8,409,076 B2 * | 4/2013 | Pang ............... A61B 10/0233 |
| | | | 600/109 |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg et al. |
| 8,556,919 B2 | 10/2013 | Aguirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierney et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |
| 8,685,043 B2 | 4/2014 | Jugenheimer et al. |
| 8,758,394 B2 | 6/2014 | Zimmerling et al. |
| 8,764,769 B1 | 7/2014 | Rodriguez-Navarro et al. |
| 8,790,245 B2 | 7/2014 | Rodriguez Fernandez et al. |
| 8,820,602 B2 | 9/2014 | Walberg et al. |
| 8,827,891 B2 | 9/2014 | Roberts |
| 8,828,024 B2 | 9/2014 | Farritor et al. |
| 8,894,574 B2 | 11/2014 | Ellman |
| 8,926,656 B2 | 1/2015 | Palermo et al. |
| 8,944,997 B2 | 2/2015 | Fernandez et al. |
| 8,968,332 B2 | 3/2015 | Farritor et al. |
| 8,968,356 B2 | 3/2015 | Mueller |
| 9,011,468 B2 | 4/2015 | Ketai et al. |
| 9,033,957 B2 | 5/2015 | Cadeddu et al. |
| 9,044,256 B2 | 6/2015 | Cadeddu et al. |
| 9,339,285 B2 | 5/2016 | Rodriguez-Navarro et al. |
| 9,386,973 B2 | 7/2016 | Deutch |
| 9,561,031 B2 | 2/2017 | Heinrich et al. |
| 9,627,120 B2 | 4/2017 | Scott et al. |
| 9,844,391 B2 | 12/2017 | Rodriguez Fernandez et al. |
| 9,962,148 B2 | 5/2018 | Deutch |
| 9,974,546 B2 | 5/2018 | Rodriguez Fernandez et al. |
| 10,010,370 B2 | 7/2018 | Rodriguez-Navarro et al. |
| 10,130,381 B2 | 11/2018 | Rodriguez-Navarro et al. |
| 10,143,459 B2 | 12/2018 | Heftman |
| 10,335,134 B2 | 7/2019 | Deutch |
| 10,537,348 B2 | 1/2020 | Rodriguez-Navarro et al. |
| 10,905,511 B2 * | 2/2021 | Rodriguez-Navarro ................. |
| | | | A61B 34/73 |
| 11,020,137 B2 | 6/2021 | Rodriguez-Navarro |
| 11,357,525 B2 | 6/2022 | Rodriguez-Navarro et al. |
| 11,413,025 B2 | 8/2022 | Deutch |
| 11,413,026 B2 | 8/2022 | Deutch |
| 11,583,354 B2 | 2/2023 | Rodriguez-Navarro et al. |
| 11,730,476 B2 | 8/2023 | Rodriguez-Navarro et al. |
| 11,751,965 B2 | 9/2023 | Rodriguez-Navarro et al. |
| 2001/0038683 A1 | 11/2001 | Ritter et al. |
| 2002/0100486 A1 | 8/2002 | Creighton, IV et al. |
| 2002/0107533 A1 | 8/2002 | Solingen |
| 2002/0116043 A1 | 8/2002 | Garibaldi et al. |
| 2002/0173805 A1 | 11/2002 | Matsuno et al. |
| 2003/0114731 A1 | 6/2003 | Cadeddu et al. |
| 2003/0125752 A1 | 7/2003 | Werp et al. |
| 2003/0181945 A1 | 9/2003 | Opolski et al. |
| 2003/0208185 A1 | 11/2003 | Sheffer et al. |
| 2004/0044295 A1 * | 3/2004 | Reinert ............ A61B 34/20 |
| | | | 600/587 |
| 2004/0050395 A1 * | 3/2004 | Ueda ............ A61B 34/73 |
| | | | 128/899 |
| 2004/0064153 A1 | 4/2004 | Creighton, IV et al. |
| 2004/0068173 A1 | 4/2004 | Viswanathan |
| 2004/0158972 A1 | 8/2004 | Creighton, IV et al. |
| 2004/0172057 A1 | 9/2004 | Guillebon et al. |
| 2004/0186347 A1 * | 9/2004 | Shose ............ A61B 34/20 |
| | | | 600/102 |
| 2004/0199074 A1 | 10/2004 | Ritter et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0085696 A1 * | 4/2005 | Uchiyama ........ A61B 1/00158 |
| | | | 600/160 |
| 2005/0113628 A1 | 5/2005 | Creighton et al. |
| 2005/0131390 A1 | 6/2005 | Heinrich et al. |
| 2005/0165449 A1 | 7/2005 | Cadeddu et al. |
| 2005/0220583 A1 | 10/2005 | Lutz |
| 2005/0250988 A1 | 11/2005 | Ewers et al. |
| 2005/0251183 A1 | 11/2005 | Buckman et al. |
| 2005/0277975 A1 | 12/2005 | Saadat et al. |

(56) References Cited

U.S. PATENT DOCUMENTS

| | | |
|---|---|---|
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | Bleich et al. |
| 2006/0116714 A1 | 6/2006 | Sepetka et al. |
| 2006/0149135 A1 | 7/2006 | Paz |
| 2006/0152309 A1* | 7/2006 | Mintchev .............. A61B 5/073 335/58 |
| 2006/0228421 A1 | 10/2006 | Seeney et al. |
| 2006/0241691 A1 | 10/2006 | Wilk |
| 2006/0247522 A1 | 11/2006 | Mcgee |
| 2006/0276738 A1 | 12/2006 | Becker |
| 2006/0293566 A1 | 12/2006 | Brown |
| 2007/0004958 A1 | 1/2007 | Ohdaira |
| 2007/0016010 A1 | 1/2007 | Creighton, IV et al. |
| 2007/0027458 A1 | 2/2007 | Sixto, Jr. et al. |
| 2007/0043359 A1 | 2/2007 | Altarac et al. |
| 2007/0073102 A1 | 3/2007 | Matsuno et al. |
| 2007/0135678 A1 | 6/2007 | Suzuki |
| 2007/0135685 A1 | 6/2007 | Cuschieri |
| 2007/0135802 A1 | 6/2007 | Suzuki |
| 2007/0135803 A1 | 6/2007 | Belson |
| 2007/0156028 A1 | 7/2007 | Van Lue et al. |
| 2007/0191670 A1 | 8/2007 | Spector |
| 2007/0221233 A1* | 9/2007 | Kawano ................ A61B 34/73 128/899 |
| 2007/0255273 A1 | 11/2007 | Fernandez et al. |
| 2007/0270629 A1 | 11/2007 | Charles |
| 2007/0282311 A1 | 12/2007 | Scott et al. |
| 2008/0081883 A1 | 4/2008 | King, II et al. |
| 2008/0097496 A1 | 4/2008 | Chang et al. |
| 2008/0108860 A1 | 5/2008 | Bell et al. |
| 2008/0134474 A1 | 6/2008 | Uryasov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Cadeddu et al. |
| 2008/0300458 A1* | 12/2008 | Kim ..................... A61B 5/064 600/118 |
| 2009/0005636 A1 | 1/2009 | Pang et al. |
| 2009/0004324 A1 | 2/2009 | Dominguez et al. |
| 2009/0043246 A1* | 2/2009 | Dominguez .......... H01F 7/0252 604/21 |
| 2009/0054909 A1 | 2/2009 | Farritor et al. |
| 2009/0062772 A1 | 3/2009 | Wakeford et al. |
| 2009/0076536 A1 | 3/2009 | Rentschler et al. |
| 2009/0137984 A1 | 5/2009 | Minnelli |
| 2009/0187074 A1 | 7/2009 | Saadat et al. |
| 2009/0192344 A1 | 7/2009 | Bakos et al. |
| 2009/0222029 A1 | 9/2009 | Gordin et al. |
| 2009/0026771 A1 | 10/2009 | Baskett |
| 2009/0267717 A1 | 10/2009 | Baskett |
| 2009/0318762 A1* | 12/2009 | Segawa ................ A61B 1/041 600/118 |
| 2010/0010306 A1* | 1/2010 | Kawano ............... A61B 1/0684 600/118 |
| 2010/0030026 A1 | 2/2010 | Uchiyama et al. |
| 2010/0036394 A1* | 2/2010 | Mintz ................... A61B 1/313 606/130 |
| 2010/0036399 A1 | 2/2010 | Viola |
| 2010/0081876 A1 | 4/2010 | Linenkugel et al. |
| 2010/0105984 A1 | 4/2010 | Brewer et al. |
| 2010/0113872 A1* | 5/2010 | Asada ................ A61B 17/3478 600/102 |
| 2010/0114126 A1 | 5/2010 | Neff |
| 2010/0137845 A1* | 6/2010 | Ramstein ............... A61B 17/29 606/1 |
| 2010/0145147 A1 | 6/2010 | Pinsky et al. |
| 2010/0152539 A1* | 6/2010 | Ghabrial ............... A61B 34/73 600/118 |
| 2010/0160739 A1 | 6/2010 | Van Lue |
| 2010/0168523 A1 | 7/2010 | Ducharme |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0237206 A1 | 9/2010 | Barker |
| 2010/0256636 A1 | 10/2010 | Fernandez et al. |
| 2010/0268254 A1 | 10/2010 | Golden et al. |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodriques et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1* | 9/2011 | Viola ..................... A61B 34/70 600/227 |
| 2011/0230869 A1 | 9/2011 | Altamirano |
| 2011/0276941 A1 | 11/2011 | Oi |
| 2011/0283822 A1 | 11/2011 | Cadeddu et al. |
| 2011/0284014 A1 | 11/2011 | Cadeddu et al. |
| 2011/0285488 A1* | 11/2011 | Scott ..................... A61B 34/76 335/306 |
| 2011/0295067 A1 | 12/2011 | Rodriguez Fernandez et al. |
| 2011/0306840 A1 | 12/2011 | Allen et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078292 A1 | 3/2012 | Banju |
| 2012/0008535 A1 | 4/2012 | Cadeddu et al. |
| 2012/0085358 A1 | 4/2012 | Cadeddu et al. |
| 2012/0101488 A1 | 4/2012 | Aldridge et al. |
| 2012/0116148 A1 | 5/2012 | Weinberg et al. |
| 2012/0227748 A1 | 9/2012 | Sanders |
| 2012/0238796 A1 | 9/2012 | Conlon |
| 2012/0330089 A1 | 12/2012 | Ritter et al. |
| 2013/0030462 A1 | 1/2013 | Keating et al. |
| 2013/0066304 A1 | 3/2013 | Belson et al. |
| 2013/0085341 A1 | 4/2013 | Nobis et al. |
| 2013/0090666 A1 | 4/2013 | Hess et al. |
| 2013/0109267 A1 | 5/2013 | Schweikardt et al. |
| 2013/0110128 A1 | 5/2013 | Schostek et al. |
| 2013/0123828 A1 | 5/2013 | Culmer et al. |
| 2013/0158348 A1 | 6/2013 | Nobis et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0172672 A1* | 7/2013 | Iddan ..................... A61B 1/041 600/109 |
| 2013/0172906 A1 | 7/2013 | Olson et al. |
| 2013/0226226 A1 | 8/2013 | Garrison et al. |
| 2013/0245356 A1 | 9/2013 | Fernandez et al. |
| 2013/0253256 A1 | 9/2013 | Griffith et al. |
| 2013/0253275 A1 | 9/2013 | Ransden et al. |
| 2013/0253550 A1 | 9/2013 | Beisel et al. |
| 2013/0267788 A1 | 10/2013 | Duan et al. |
| 2013/0289579 A1 | 10/2013 | Yeung et al. |
| 2013/0289617 A1 | 10/2013 | Suzuki et al. |
| 2013/0289768 A1* | 10/2013 | Yeung ................... A61B 34/73 700/258 |
| 2013/0303851 A1 | 11/2013 | Griffith et al. |
| 2014/0066695 A1 | 3/2014 | Deutch |
| 2014/0084761 A1 | 3/2014 | Scott et al. |
| 2014/0135616 A1* | 5/2014 | Stein ..................... A61B 34/30 600/424 |
| 2014/0176797 A1 | 6/2014 | Silva et al. |
| 2014/0187857 A1 | 7/2014 | Wilson et al. |
| 2014/0243586 A1 | 8/2014 | Rohaninejad et al. |
| 2014/0243597 A1 | 8/2014 | Weisenburgh, II et al. |
| 2014/0257370 A1 | 9/2014 | Taylor et al. |
| 2014/0276335 A1 | 9/2014 | Pate |
| 2014/0277104 A1 | 9/2014 | Rodriguez-Navarro et al. |
| 2014/0350574 A1 | 11/2014 | Farritor et al. |
| 2014/0358162 A1 | 12/2014 | Valdastri et al. |
| 2014/0358229 A1 | 12/2014 | Bergs et al. |

(56) References Cited

U.S. PATENT DOCUMENTS

| | | | |
|---|---|---|---|
| 2015/0012010 A1* | 1/2015 | Adler | A61B 34/35 606/130 |
| 2015/0018614 A1 | 1/2015 | Duan et al. | |
| 2015/0141750 A1* | 5/2015 | Iddan | A61B 34/73 600/104 |
| 2016/0038135 A1 | 2/2016 | Deutch | |
| 2016/0120613 A1 | 5/2016 | Cadeddu et al. | |
| 2016/0228138 A1* | 8/2016 | Rodriguez-Navarro | A61B 17/2812 |
| 2016/0302811 A1 | 10/2016 | Rodriguez-Navarro et al. | |
| 2018/0092703 A1 | 4/2018 | Rodriguez-Navarro et al. | |
| 2018/0153633 A1* | 6/2018 | Rodriguez-Navarro | A61B 17/0218 |
| 2018/0271550 A1 | 9/2018 | Rodriguez-Navarro | |
| 2018/0271603 A1* | 9/2018 | Nir | A61B 34/25 |
| 2018/0296289 A1* | 10/2018 | Rodriguez-Navarro | A61B 1/126 |
| 2018/0325604 A1* | 11/2018 | Atarot | A61B 5/7475 |
| 2019/0133631 A1 | 5/2019 | Rodriguez-Navarro et al. | |
| 2019/0269394 A1 | 9/2019 | Deutch | |
| 2019/0350575 A1 | 11/2019 | Deutch | |
| 2020/0289140 A1 | 9/2020 | Rodriguez-Navarro et al. | |
| 2021/0290330 A1 | 9/2021 | Rodriguez-Navarro et al. | |
| 2022/0015789 A1 | 1/2022 | Rodriguez-Navarro | |
| 2023/0021246 A1 | 1/2023 | Rodriguez-Navarro et al. | |
| 2023/0106676 A1 | 4/2023 | Deutch | |
| 2023/0277266 A1 | 9/2023 | Rodriguez-Navarro et al. | |
| 2024/0108345 A1 | 4/2024 | Rodriguez-Navarro et al. | |
| 2024/0156556 A1 | 5/2024 | Rodriguez-Navarro et al. | |

FOREIGN PATENT DOCUMENTS

| | | | | |
|---|---|---|---|---|
| CA | 2733465 A1 | 9/2011 | | |
| CN | 2244381 Y | 1/1997 | | |
| CN | 101090672 A | 12/2007 | | |
| CN | 201079412 Y | 7/2008 | | |
| CN | 201091596 Y | 7/2008 | | |
| CN | 101534725 A | 9/2009 | | |
| CN | 102068288 A | 5/2011 | | |
| CN | 102355865 A | 2/2012 | | |
| CN | 203953720 U | 11/2014 | | |
| DE | 42 12 430 A1 | 10/1993 | | |
| DE | 19534618 A1 | 3/1997 | | |
| DE | 10 2005 006 705 A1 | 8/2006 | | |
| DE | 10-2010-010417 A1 | 9/2011 | | |
| EP | 1 797 823 A1 | 6/2007 | | |
| EP | 1 972 284 A2 | 9/2008 | | |
| EP | 2 012 697 A2 | 1/2009 | | |
| EP | 2 355 699 A2 | 8/2011 | | |
| EP | 2 366 357 A1 | 9/2011 | | |
| EP | 2 381 873 A2 | 11/2011 | | |
| EP | 2 391 277 | 12/2011 | | |
| EP | 1 942 810 B1 | 8/2012 | | |
| EP | 2 571 443 A2 | 3/2013 | | |
| EP | 2 595 548 | 5/2013 | | |
| EP | 2 842 511 A1 | 3/2015 | | |
| JP | 09-192137 A | 7/1997 | | |
| JP | 2004-357816 A | 12/2004 | | |
| JP | 2005-021576 A | 1/2005 | | |
| JP | 4320214 B2 | 8/2009 | | |
| JP | 2009-538699 A | 11/2009 | | |
| WO | WO-00/51500 A1 | 9/2000 | | |
| WO | WO-2005/004734 A1 | 1/2005 | | |
| WO | WO-2005032370 A1 * | 4/2005 | | A61B 5/6885 |
| WO | WO-2006/071120 A1 | 7/2006 | | |
| WO | WO-2007/067231 A1 | 6/2007 | | |
| WO | WO-2007/130382 A2 | 11/2007 | | |
| WO | WO-2007/130382 A3 | 11/2007 | | |
| WO | WO-2007/142977 A2 | 12/2007 | | |
| WO | WO-2007/142977 A3 | 12/2007 | | |
| WO | WO-2007/143162 A2 | 12/2007 | | |
| WO | WO-2007/143162 A3 | 12/2007 | | |
| WO | WO-2007/143170 A2 | 12/2007 | | |
| WO | WO-2007/143170 A3 | 12/2007 | | |
| WO | WO-2008/039237 A1 | 4/2008 | | |
| WO | WO-2008/085919 A2 | 7/2008 | | |
| WO | WO-2008/085919 A3 | 7/2008 | | |
| WO | WO-2008/131128 A1 | 10/2008 | | |
| WO | WO-2009/008865 A1 | 1/2009 | | |
| WO | WO-2009/019288 A2 | 2/2009 | | |
| WO | WO-2009/019288 A3 | 2/2009 | | |
| WO | WO-2009/070743 A1 | 6/2009 | | |
| WO | WO-2010/056716 A2 | 5/2010 | | |
| WO | WO-2010/056716 A3 | 5/2010 | | |
| WO | WO-2010/077561 A1 | 7/2010 | | |
| WO | WO-2010/083480 A2 | 7/2010 | | |
| WO | WO-2010/083480 A3 | 7/2010 | | |
| WO | WO-2010/089635 A1 | 8/2010 | | |
| WO | WO-2011/044468 A2 | 4/2011 | | |
| WO | WO-2011/044468 A3 | 4/2011 | | |
| WO | WO-2011/044471 A2 | 4/2011 | | |
| WO | WO-2011/044471 A3 | 4/2011 | | |
| WO | WO-2011/091483 A1 | 8/2011 | | |
| WO | WO-2011/146691 A2 | 11/2011 | | |
| WO | WO-2011/146691 A3 | 11/2011 | | |
| WO | WO2011/146698 A2 | 11/2011 | | |
| WO | WO-2011/146698 A3 | 11/2011 | | |
| WO | WO-2011/146709 A2 | 11/2011 | | |
| WO | WO-2011/146709 A3 | 11/2011 | | |
| WO | WO-2012/010910 A1 | 1/2012 | | |
| WO | WO-2012/031114 A2 | 3/2012 | | |
| WO | WO-2012/031114 A3 | 3/2012 | | |
| WO | WO-2012/033925 A1 | 3/2012 | | |
| WO | WO-2012/048102 A2 | 4/2012 | | |
| WO | WO-2012/048102 A3 | 4/2012 | | |
| WO | WO-2013/096470 A1 | 6/2013 | | |
| WO | WO-2014/133751 A1 | 9/2014 | | |
| WO | WO-2014/159023 A1 | 10/2014 | | |
| WO | WO-2014/163872 A1 | 10/2014 | | |
| WO | WO-2015/112645 A1 | 7/2015 | | |
| WO | WO-2015142953 A1 * | 9/2015 | | A61B 34/30 |
| WO | WO-2016/168380 A1 | 10/2016 | | |

OTHER PUBLICATIONS

Non-Final Office Action mailed on Dec. 22, 2020, for U.S. Appl. No. 16/149,576, filed Oct. 2, 2018, 10 pages.

Notice of Allowance mailed on Sep. 29, 2020, for U.S. Appl. No. 15/728,302, filed Oct. 9, 2017, 8 pages.

Notice of Allowance mailed on Feb. 5, 2021, for U.S. Appl. No. 15/926,578, filed Mar. 20, 2018, 9 pages.

Supplemental Notice of Allowability mailed on Dec. 18, 2020, for U.S. Appl. No. 15/728,302, filed Oct. 9, 2017, 3 pages.

Best, S.L. et al. (2010). "Development of magnetic anchoring and guidance systems for minimally invasive surgery," Indian J. of Urology 26:418-422.

Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.

Best, S.L. et al. (2008). "Maximizing Coupling Strength of Magnetically Anchored Notes Instruments: How Thick Can We Go?" Surgical Endoscopy, vol. 22: S241.

Cadeddu, J.A. et al. (2002). "Transabdominal magnetic anchoring system for trocar-less laparoscopic surgery," J. of Urology, vol. 167, No. 4, Supplement, Abstract No. 16, 1 total page.

Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.

Dominguez, G. et al. (2009). "Retraction and triangulation with neodymium magnetic forceps for single-port laparoscopic cholecystectomy," Surg. Endosc. 23:1660-1666.

Duchene, D.A. et al. (2004). "Magnetic positioning system for trocarless laparoscopic instruments," J. of Endourology 18:693.

Extended European Search Report mailed on Aug. 22, 2019, for EP Application No. 17 736 483.3, filed on Jan. 6, 2017, 8 pages.

Fernandez, R. et al. (2012). "Determining a Performance Envelope for Capture of Kidney Stones Functionalized with Superparamagnetic Particles," Journal of Endourology, 26(9):1227-30.

(56) References Cited

OTHER PUBLICATIONS

Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, BED vol. 55, pp. 157-158.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, P246, National Harbor, MD, Apr. 2010.
Non-Final Office Action mailed on Mar. 3, 2020, for U.S. Appl. No. 15/728,302, filed Oct. 9, 2017, 14 pages.
Non-Final Office Action mailed on Mar. 6, 2020, for U.S. Appl. No. 15/926,578, filed Mar. 20, 2018, 9 pages.
Park, S. et al. (2007). "Trocar-less instrumentation for laparoscopy magnetic positioning of intra-abdominal camera and retractor," Surgical Technique 245:379-384.
Raman, J. (2009). "Complete Transvaginal Notes Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Minimally Invasive Robotic Association (MIRA) Conference on Robotic Surgery, Innsbruck, Austria, Dec. 2005.
Scott, D.J. et al. (2007). "Completely transvaginal Notes cholecystectomy using magnetically anchored instruments," Surg. Endosc. 21:2308-2316.
Scott, D. et al. (2008). "Optimizing Magnetically Anchored Camera, Light Source, Graspers, and Cautery Dissector for Transvaginal Notes Cholecystectomy," Surgical Endoscopy 22:S244.
Scott, D. et al. (2008). "A Randomized Comparison of Laparoscopic, Flexible Endoscopic, and Wired and Wireless Magnetic Notes Cameras on Ex-Vivo and In-Vivo Surgical Performance," Gastrointestinal Endoscopy, vol. 67: AB115.
Scott, D. et al. (2008). "Transvaginal Single Access "Pure" Notes Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.
Scott, D. et al. (2007). "Short-Term Survival Outcomes Following Transvaginal Notes Cholecystectomy Using Magnetically Anchored Instruments," Gastrointestinal Endoscopy, vol. 65: AB109.
Swain, C. et al. (2008). "Linear Stapler Formation of Ileo-Rectal, Entero-Enteral and Gastrojejunal Anastomoses During Dual and Single Access "Pure" Notes Procedures: Methods, Magnets and Stapler Modifications," Gastrointestinal Endoscopy, vol. 67: AB119.
Swain, P. et al. (2008). "Wireless Endosurgery for Notes," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-858.
Tang, S. (2008). "Live Video Manipulator for Endoscopy and Notes," Gastrointestinal Endoscopy 68:559-564.
Tillander, H. (1951). "Magnetic guidance of a catheter with articulated steel tip," Acta Radiologica pp. 62-64.
Zeltser, I.S. et al. (2007). "Single trocar laparoscopic nephrectomy using magnetic anchoring and guidance system in the porcine model," J. of Urology 178:1-4.
Final Office Action mailed on Feb. 26, 2019, for U.S. Appl. No. 15/195,898, filed Jun. 28, 2016, 9 pages.
International Search Report mailed on Apr. 3, 2017, for PCT Application No. PCT/US2017/012628, filed on Jan. 6, 2017, 2 pages.
Written Opinion of the International Searching Authority mailed on Apr. 3, 2017, for PCT Application No. PCT/US2017/012628, filed on Jan. 6, 2017, 7 pages.
Non-Final Office Action mailed on Sep. 17, 2019, for U.S. Appl. No. 15/728,297, filed Oct. 9, 2017, 8 pages.
Notice of Allowance mailed on Sep. 11, 2019, for U.S. Appl. No. 15/195,898, filed Jun. 28, 2016, 9 pages.
Notice of Allowance mailed on Nov. 26, 2019, for U.S. Appl. No. 15/195,898, filed Jun. 28, 2016, 6 pages.
U.S. Appl. No. 61/113,495, filed Nov. 25, 2008, by Fernandez et al.
Dominguez (2007). "Colecistectomia con un trocar asistida por imanes de neodimio. Reporte de un caso." Asociacion Mexicana de Cirugia Endo. vol. 8. No. 4, pp. 172-176 (with English Abstract).
Extended European Search Report mailed on Jul. 20, 2016, for EP Application No. 14 778 895.4, filed on Feb. 25, 2014, 7 pages.
Extended European Search Report mailed on Dec. 20, 2016, for EP Application No. 09 839 564.3, filed on Oct. 1, 2009, 11 pages.
Extended European Search Report mailed on Sep. 27, 2017, for EP Application No. 15 741 055.6, filed on Jan. 21, 2015, 9 pages.
Extended European Search Report mailed on Oct. 30, 2018, for EP Application No. 16 780 691.8, filed on Apr. 13, 2016, 6 pages.
Extended European Search Report mailed on Nov. 26, 2018, for EP Application No. 16 780 688.4, filed on Sep. 26, 2017, 9 pages.
Final Office Action mailed on Sep. 16, 2016, for U.S. Appl. No. 14/704,828, filed May 5, 2015, 10 pages.
Final Office Action mailed on Jan. 25, 2016, for U.S. Appl. No. 14/337,082, filed Jul. 21, 2014, 9 pages.
Final Office Action mailed on Dec. 28, 2016, for U.S. Appl. No. 14/200,302, filed Mar. 7, 2014, 15 pages.
Final Office Action mailed on Sep. 6, 2017, for U.S. Appl. No. 14/200,302, filed Mar. 7, 2014, 9 pages.
Final Office Action mailed on Mar. 7, 2018, for U.S. Appl. No. 15/098,262, filed Apr. 13, 2016, 10 pages.
International Search Report mailed on Jul. 30, 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report mailed on May 4, 2015, for PCT Application No. PCT/US2015/012319, filed on Jan. 21, 2015, 2 pages.
International Search Report mailed on Jul. 18, 2014, for PCT Application No. PCT/US2014/018307, filed on Feb. 25, 2014, 4 pages.
International Search Report mailed on Jul. 15, 2016, for PCT Application No. PCT/US2016/027385, filed on Apr. 13, 2016, 2 pages.
International Search Report mailed on Aug. 22, 2016, for PCT Application No. PCT/US2016/027390, filed on Apr. 13, 2016, 4 pages.
Non-Final Office Action mailed on May 25, 2016, for U.S. Appl. No. 14/200,302, filed Mar. 7, 2014, 12 pages.
Non-Final Office Action mailed on May 21, 2013 for U.S. Appl. No. 13/132,185, filed Aug. 17, 2011, 18 pages.
Non-Final Office Action mailed on Jul. 21, 2016, for U.S. Appl. No. 14/337,082, filed Jul. 21, 2014, 9 pages.
Non-Final Office Action mailed on Jul. 13, 2015, for U.S. Appl. No. 14/337,082, filed Jul. 21, 2014, 10 pages.

(56) References Cited

OTHER PUBLICATIONS

Non-Final Office Action mailed on Jan. 25, 2016, for U.S. Appl. No. 14/704,828, filed May 5, 2015, 9 pages.
Non-Final Office Action mailed on Jul. 14, 2015, for U.S. Appl. No. 14/704,828, filed May 5, 2015, 10 pages.
Non-Final Office Action mailed on Oct. 24, 2013, for U.S. Appl. No. 14/019,370, filed Sep. 5, 2013, 7 pages.
Non-Final Office Action mailed on Oct. 22, 2015, for U.S. Appl. No. 14/019,404, filed Sep. 5, 2013, 6 pages.
Non-Final Office Action mailed on May 22, 2017, for U.S. Appl. No. 14/200,302, filed Mar. 7, 2014, 14 pages.
Non-Final Office Action mailed on May 3, 2017, for U.S. Appl. No. 14/704,828, filed May 5, 2015, 8 pages.
Non-Final Office Action mailed on Jul. 24, 2017, for U.S. Appl. No. 15/098,262, filed Apr. 13, 2016, 9 pages.
Non-Final Office Action mailed on Jun. 29, 2018, for U.S. Appl. No. 15/195,898, filed Jun. 28, 2016, 9 pages.
Notice of Allowance mailed on Feb. 14, 2014, for U.S. Appl. No. 14/019,370, filed Sep. 5, 2013, 7 pages.
Notice of Allowance mailed on Mar. 14, 2014, for U.S. Appl. No. 13/132,185, filed Aug. 17, 2011, 7 pages.
Notice of Allowance mailed on Mar. 14, 2016, for U.S. Appl. No. 14/019,404, filed Sep. 5, 2013, 7 pages.
Notice of Allowance mailed on May 3, 2017, for U.S. Appl. No. 14/337,082, filed Jul. 21, 2014, 7 pages.
Notice of Allowance mailed on Aug. 25, 2017, for U.S. Appl. No. 14/337,082, filed Jul. 21, 2014, 7 pages.
Notice of Allowance mailed on Nov. 22, 2017, for U.S. Appl. No. 14/200,302, filed Mar. 7, 2014, 5 pages.
Notice of Allowance mailed on Jan. 19, 2018, for U.S. Appl. No. 14/704,828, filed May 5, 2015, 7 pages.
Notice of Allowance mailed on Aug. 24, 2018, for U.S. Appl. No. 15/098,262, filed Apr. 13, 2016, 9 pages.
Wikipedia (2015). "Stainless Steel," retrieved from https://en.wikipedia.org/wiki/Stainless_steel, 13 pages.
Written Opinion of the International Searching Authority mailed on Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010.
Written Opinion of the International Searching Authority mailed on Jul. 18, 2014, for PCT Application No. PCT/US2014/018307, filed on Feb. 25, 2014, 5 pages.
Written Opinion of the International Searching Authority mailed on May 4, 2015, for PCT Application No. PCT/US2015/012319, filed on Jan. 21, 2015, 5 pages.
Written Opinion of the International Searching Authority mailed on Jul. 15, 2016, for PCT Application No. PCT/US2016/027385, filed on Apr. 13, 2016, 11 pages.
Written Opinion of the International Searching Authority mailed on Aug. 22, 2016, for PCT Application No. PCT/US2016/027390, filed on Apr. 13, 2016, 9 pages.
Aesculap, "Endoscopic Vascular surgery in the pelvic region," B/Braun, Aesculap AG & Co.KG, Catalog, 48 pages, 2006, document can be accessed at https://docplayer.net/22042174-Aesculap-endoscopic-technology-endoscopic-vascular-surgery-in-the-pelvic-region.html.
Extended European Search Report mailed on May 31, 2013, for EP Application No. 08 853 840.0, filed on Nov. 26, 2008, 11 pages.
Final Office Action mailed on Sep. 3, 2021, for U.S. Appl. No. 16/149,576, filed Oct. 2, 2018, 14 pages.
International Search Report mailed on Apr. 9, 2009, for PCT Application No. PCT/US2008/084991, filed on Nov. 26, 2008, 3 pages.
Milki et al. (1998). Vaginal ultrasound probe coverage leakage: implications for patient care, fertility and sterility, American Society for Reproductive Medicine, vol. 69, No. 3.
Non-Final Office Action mailed on Apr. 29, 2021, for U.S. Appl. No. 16/419,363, filed May 22, 2019, 9 pages.
Non-Final Office Action mailed on Apr. 15, 2021, for U.S. Appl. No. 16/528,878, filed Aug. 1, 2019, 6 pages.
Non-Final Office Action mailed on Sep. 15, 2021, for U.S. Appl. No. 15/728,297, filed Oct. 9, 2017, 11 pages.
Odwin et al. (1990). Prove covers and disinfectants for transvaginal transducers, JDMS, 6:130-135.
Written Opinion of the International Searching Authority mailed on Apr. 9, 2009, for PCT Application No. PCT/US2008/084991, filed on Nov. 26, 2008, 12 pages.
Extended European Search Report mailed on Jan. 4, 2022, for EP Application No. 21 189 505.7, filed on Apr. 13, 2016, 10 pages.
Extended European Search Report mailed on Jan. 18, 2022, for EP Application No. 21 187 437.5, filed on Apr. 13, 2016, 6 pages.
Extended European Search Report mailed on Feb. 17, 2022, for EP Application No. 21 189 492.8, filed on Feb. 25, 2014, 6 pages.
Final Office Action mailed on Oct. 26, 2021, for U.S. Appl. No. 16/419,363, filed May 22, 2019, 7 pages.
Final Office Action mailed on Oct. 28, 2021, for U.S. Appl. No. 16/528,878, filed Aug. 1, 2019, 8 pages.
Final Office Action mailed on May 2, 2022, for U.S. Appl. No. 15/728,297, filed Oct. 9, 2017, 13 pages.
Notice of Allowance mailed on Feb. 14, 2022, for U.S. Appl. No. 16/149,576, filed Oct. 2, 2018, 9 pages.
Notice of Allowance mailed on Apr. 7, 2022, for U.S. Appl. No. 16/528,878, filed Aug. 1, 2019, 6 pages.
Notice of Allowance mailed on Apr. 20, 2022, for U.S. Appl. No. 16/419,363, filed May 22, 2019, 6 pages.
Extended European Search Report mailed on Jul. 22, 2019, for EP Application No. 19 151 941.2, filed on Feb. 25, 2014, 6 pages.
Notice of Allowance mailed on Oct. 19, 2022, for U.S. Appl. No. 15/728,297, filed Oct. 9, 2017, 8 pages.
Corrected Notice of Allowability mailed on Jul. 12, 2023, for U.S. Appl. No. 17/161,185, filed Jan. 28, 2021, 4 pages.
Non-Final Office Action mailed on Oct. 12, 2022, for U.S. Appl. No. 16/746,448, filed Jan. 17, 2020, 16 pages.
Non-Final Office Action mailed on Oct. 28, 2022, for U.S. Appl. No. 17/161,185, filed Jan. 28, 2021, 9 pages.
Notice of Allowance mailed on Apr. 3, 2023, for U.S. Appl. No. 16/746,448, filed Jan. 17, 2020, 12 pages.
Notice of Allowance mailed on Apr. 10, 2023, for U.S. Appl. No. 17/161,185, filed Jan. 28, 2021, 9 pages.
Final Office Action mailed on May 31, 2024, for U.S. Appl. No. 16/008,976, filed Jun. 14, 2018, 12 pages.
Non-Final Office Action mailed on Jul. 18, 2024, for U.S. Appl. No. 17/836,867, filed Jun. 9, 2022, 10 pages.
Non-Final Office Action mailed on Sep. 13, 2024, for U.S. Appl. No. 18/220,192, filed Jul. 10, 2023, 11 pages.
Notice of Allowance mailed on Aug. 14, 2024, for U.S. Appl. No. 18/346,089, filed Jun. 30, 2023, 14 pages.
Notice of Allowance mailed on Sep. 5, 2024, for U.S. Appl. No. 17/332,876, filed May 27, 2021, 7 pages.
Non-Final Office Action mailed on Feb. 16, 2024, for U.S. Appl. No. 17/332,876, filed May 27, 2021, 10 pages.

\* cited by examiner

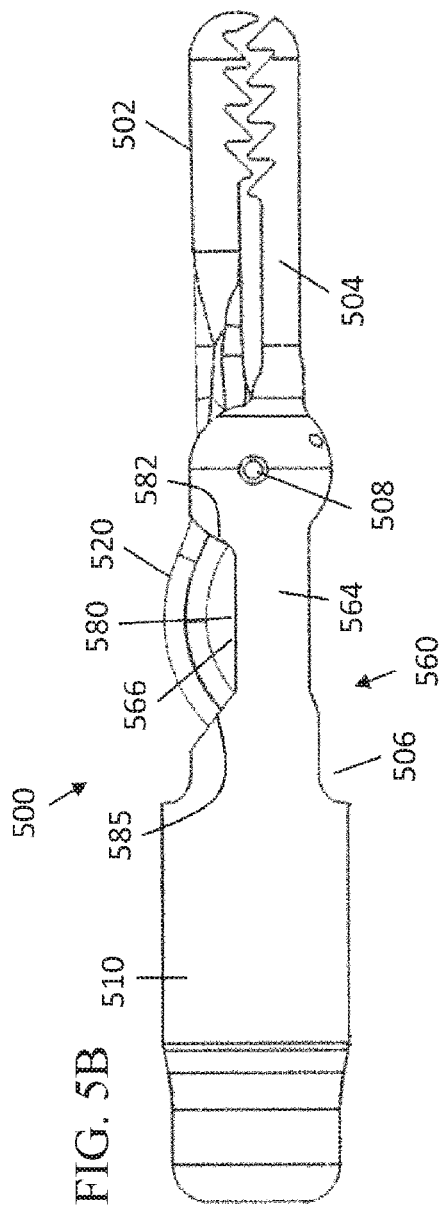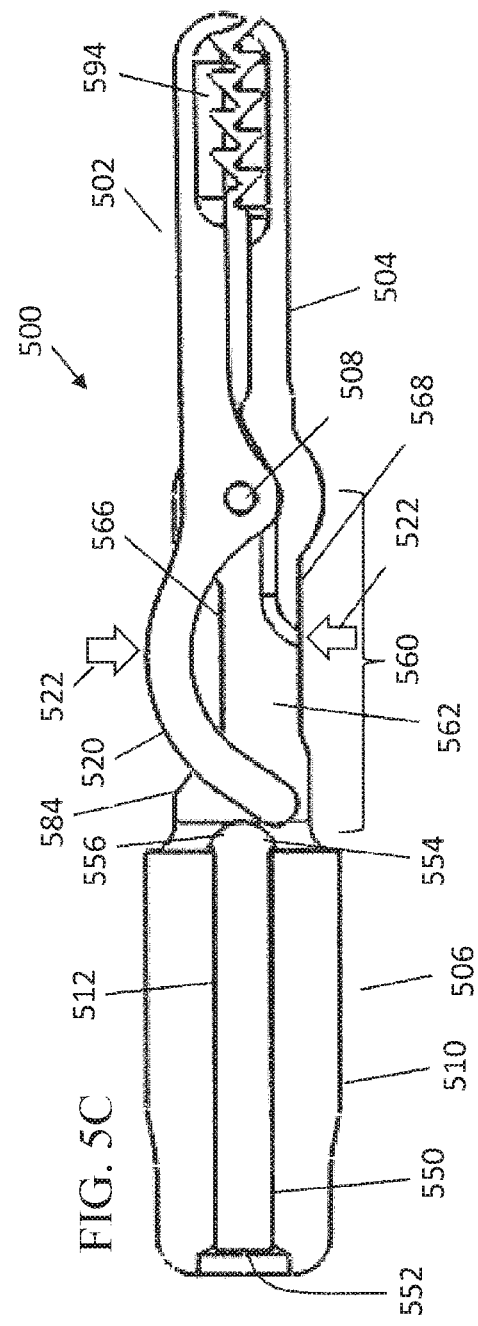

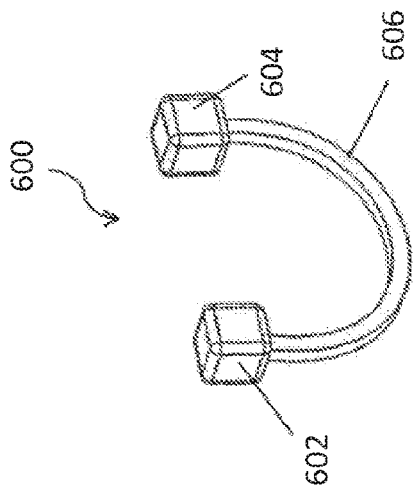
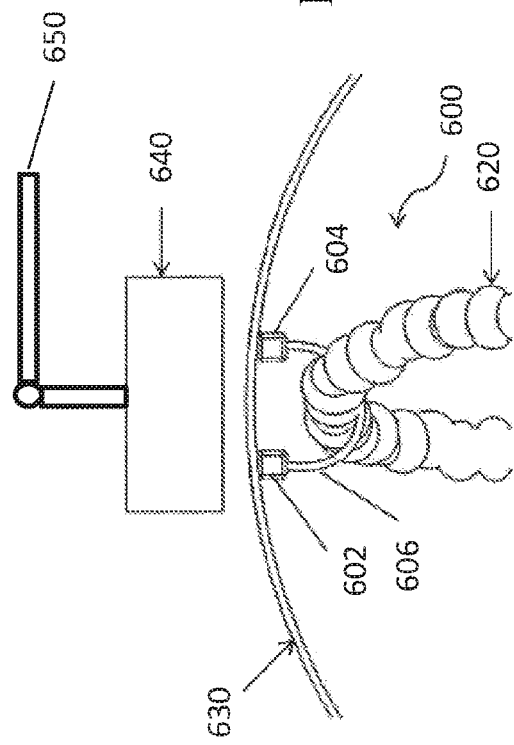
FIG. 6A
FIG. 6B

ONE-OPERATOR SURGICAL SYSTEM AND METHODS OF USE

CROSS-REFERENCE TO RELATED APPLICATIONS

This application is a continuation of International Application No. PCT/US2017/012628, filed Jan. 6, 2017, which claims priority to U.S. Provisional Application No. 62/276,752, filed Jan. 8, 2016, and titled "One-Operator Surgical System," each of which is hereby incorporated by reference in its entirety.

FIELD

The present invention is directed toward systems, devices, and methods for providing remote manipulation or visualization of tissue using a surgical system that may be operated by a single operator.

BACKGROUND

Many surgical procedures are shifting toward the use of minimally invasive approaches that are configured to minimize the number and size of incisions that are made in a patient. Minimally invasive procedures such as endoscopic, laparoscopic, and thoracoscopic procedures may be associated with lower pain, quicker post-surgical recovery, shortened hospitalization, and reduced complications when compared to open surgical procedures. During minimally invasive procedures it may be desirable to reposition or otherwise manipulate tissue, however the introduction of additional devices to engage tissue may crowd the access sites provided by incisions, which may require the formation of larger or additional access sites.

Minimally invasive robotic surgery using video is currently performed by two skilled surgeons (e.g., operators). A primary surgeon performs the surgical tasks (e.g. dissection, clipping, cutting, stapling, etc.) and a secondary surgeon assists in these functions. The primary surgeon is located at a console outside of a sterile field while the secondary surgeon is located within the sterile field in order to assist by, for example, changing the instruments coupled to a robotic surgical system. As another example, the secondary surgeon may assist the primary surgeon by holding an instrument in each hand such as an optical sensor (e.g., camera) and a retractor. Accordingly, it may be desirable to provide a surgical system having one or more devices to manipulate tissue controlled by a single operator without an assistant operator.

BRIEF SUMMARY

Described here are systems and methods useful for minimally invasive surgical procedures performed by a single operator. Generally, the systems for manipulating tissue may comprise one or more intracavity devices each configured to be advanced through an access site into a body cavity or lumen of a patient. One or more external magnetic positioning devices may be configured to magnetically couple to a respective intracavity device through tissue (e.g., through a body cavity wall). A controller may comprise a processor and memory. A display may be coupled to the controller. The controller may be configured to generate a graphical user interface on the display and control movement of the one or more intracavity devices within the body cavity or lumen.

In some variations, the controller may be configured to control the external magnetic positioning devices to magnetically hold the respective intracavity device in the body cavity or lumen. The controller is configured to move each external magnetic positioning device coupled to the intracavity device in response to the graphical user interface receiving operator input to control the intracavity device. One or more of the intracavity devices may be configured to generate an image of a portion of the body cavity or lumen, and the graphical user interface may be configured to generate an intracavity device control button using the image. In some of these variations, the image may be a real-time image. In other variations, the graphical user interface may be configured to simultaneously control two or more of the intracavity devices.

In another variation, the system for manipulating tissue may comprise one or more intracavity devices each configured to be advanced through an access site into a body cavity or lumen of a patient. One or more external magnetic positioning devices may each comprise a support arm and a magnet coupled thereto. The support arm may be configured to moveably suspend the magnet externally of the patient. The magnet may be configured to generate a magnetic field and to apply a magnetic force to a respective intracavity device. An input device may be configured to receive a control signal from an operator to control the one or more intracavity devices. A controller may be coupled to the input device. The controller may be configured to control a movement of each of the intracavity devices within the body cavity or lumen by moving the support arm and applying the magnetic force to the intracavity device, and may be configured to actuate at least one of the intracavity devices.

The system may include one or more additional features. In some variations, the input device may comprise a touch surface configured to receive the control signal from the operator. An output device may be configured to display a graphical user interface. In some of these variations, the output device may further comprise an audio device and a haptic device. In other variations, at least one of the external magnetic positioning devices comprises one or more of a proximity sensor, force sensor, and magnetic field sensor. In some variations, one or more intracavity devices may comprise a visualization device and a tissue manipulation device. In other variations, the system may further comprise a delivery device configured to releasably engage the intracavity device and actuate the intracavity device.

Also described here are methods of performing minimally invasive surgery comprising advancing one or more intracavity devices through an access site into a body cavity or lumen of a patient and magnetically coupling each of the intracavity devices to a respective positioning device. Each of the positioning devices may be located externally of the patient. Each of the intracavity devices may move within the body cavity or lumen using the respective positioning devices. Each of the intracavity devices may be controlled using a graphical user interface.

In some variations, the magnetic coupling may comprise generating a magnetic field using the positioning device. In some of these variations, moving each of the intracavity devices within the body cavity or lumen may further comprise moving the positioning device or modifying the magnetic field generated by the positioning device. In other variations, controlling each of the intracavity devices may comprise actuating at least one of the intracavity devices using the graphical user interface. The intracavity device may be held in contact with a patient cavity wall within a predetermined force threshold. In some variations, the methods may further comprise advancing a second intracavity device into the body cavity through the access site. The second intracavity device may be magnetically coupled to a second positioning device, wherein the second positioning device is located externally of the patient, and the method may further comprise controlling the first intracavity device and the second intracavity device using a graphical user interface. The first and second intracavity devices may be controlled using the graphical user interface through input from a single operator, wherein the single operator is not assisted by a second operator.

Also described here are methods of performing minimally invasive surgery comprising advancing a first intracavity device through an access site into a body cavity of a patient, advancing a second intracavity device through the access site into the body cavity, moving the first intracavity device within the body cavity, and moving the second intracavity device within the body cavity, wherein movement of the first and second intracavity devices is controlled by a single operator unassisted by a second operator. A third intracavity device may further be advanced through the access site into the body cavity, and may be moved within the body cavity, wherein movement of the first, second, and third intracavity devices is controlled by the single operator unassisted by a second operator.

BRIEF DESCRIPTION OF THE DRAWINGS

FIGS. 5A and 5B depict perspective and side views, respectively, of an illustrative variation of a grasper. FIG. 5C depicts a cross-sectional side view of the grasper shown in FIGS. 5A and 5B.

FIG. 6A depicts a perspective view of an illustrative variation of a retractor. FIG. 6B is a cross-sectional view of an illustrative variation of a surgical system having the retractor shown in FIG. 6A in a patient body cavity.

DETAILED DESCRIPTION

Described here are systems, devices, and methods for use in minimally invasive surgical procedures performed by a single operator. While the single operator may be assisted by a less skilled assistant such as a scrub nurse, the systems and methods disclosed herein do not require a second skilled operator to assist the single operator. Some of the surgical systems described herein may be used to perform surgical procedures such as a cholecystectomy, appendectomy, colectomy, hernia repair, sleeve gastrectomy or other bariatric procedures, nephrectomy, hysterectomy, oophorectomy, and lobectomy.

I. Systems and Devices

Figure 1:
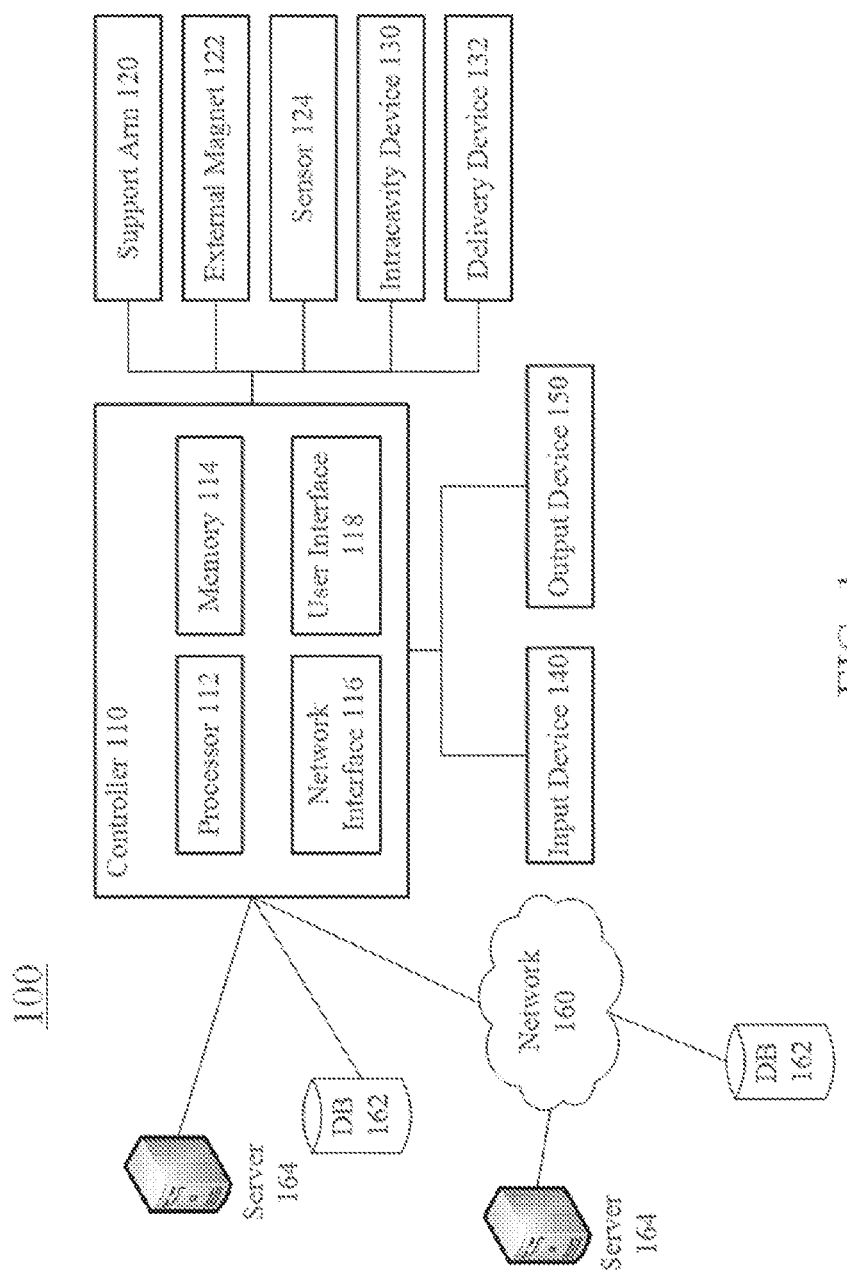
FIG. 1 is a block diagram of an illustrative variation of a surgical system.

A block diagram of an exemplary surgical system 100 is depicted in FIG. 1. The system 100 may comprise a controller 110 coupled to one or more support arms 120, external magnets 122, sensors 124, intracavity devices 130, and delivery devices 132. An operator may control the surgical system 100 using one or more input devices 140 and output devices 150 each coupled to the controller 110. In some variations, an external magnetic positioning device may comprise the support arm 120, the external magnet 122, and sensors 124. The sensors 124 may comprise one or more of a proximity sensor, force sensor, optical sensor, motion sensor, temperature sensor, biometric sensor, or the like. The intracavity device 130 may be removably coupled to the delivery device 132 to advance the intracavity device 130 into a body cavity or lumen.

The controller 110 may comprise a processor 112, memory 114, a network interface 116, and a user interface 118. The various components of the controller 110 may be coupled by one or more communication buses or signal lines (not shown). In some variations, the controller 110 may be coupled to one or more of a communication network 160, database 162, and server 164 via the network interface 116. An operator may control the system 100 through the user interface 118. For example, the controller 110 may control the movement of the support arm 120 or the magnetic field strength of the external magnet 122 through a control signal input to an input device 140. The controller 110 may also receive sensor data from one or more sensors 124. In some variations, a remote operator may monitor and/or control the system 100 from a remote location using a remote server 164 coupled to the controller 110.

Figure 2A:
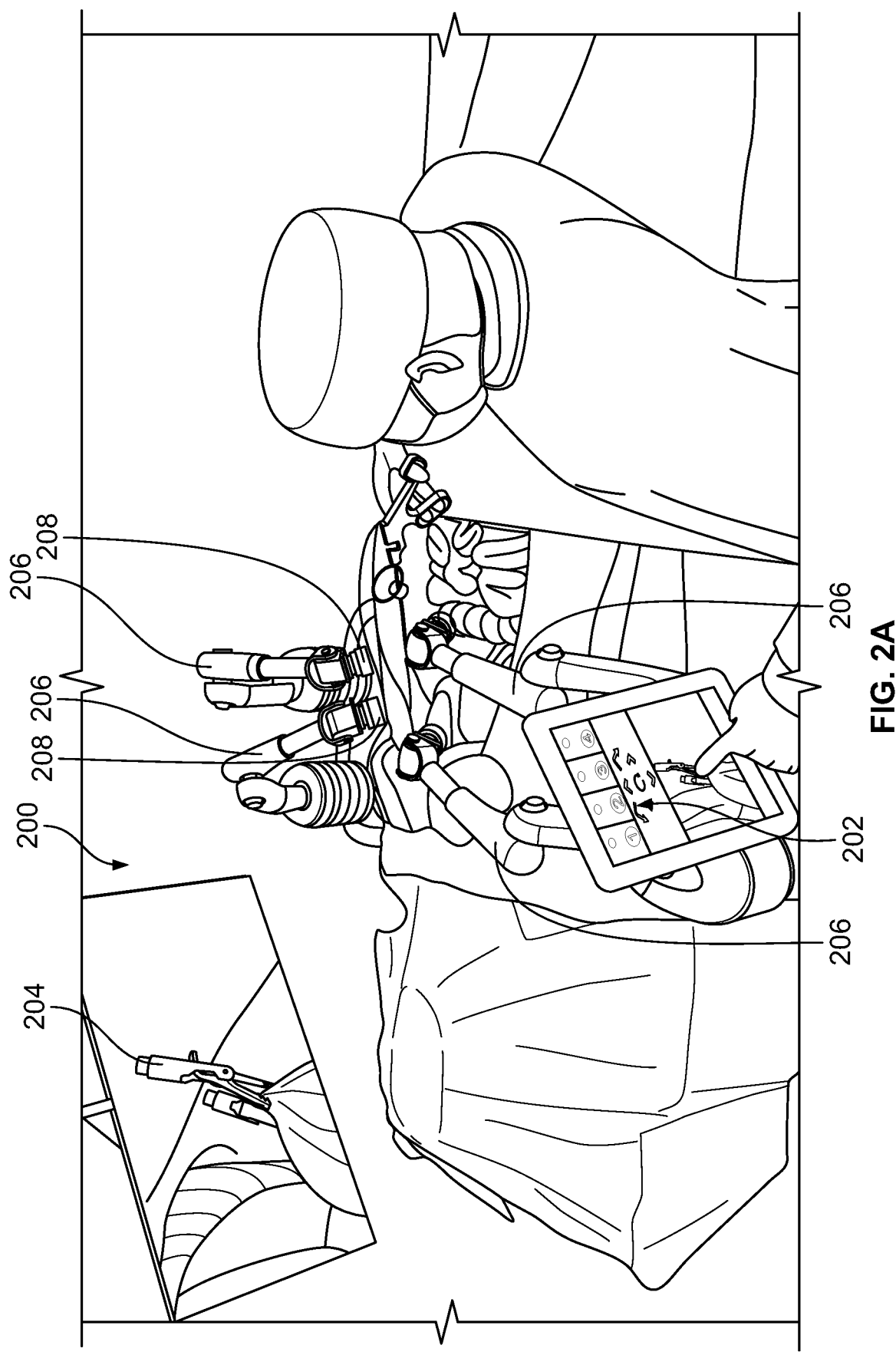
FIGS. 2A-2B depict perspective views of an illustrative variation of a surgical system, patient and operator.
Figure 2B:
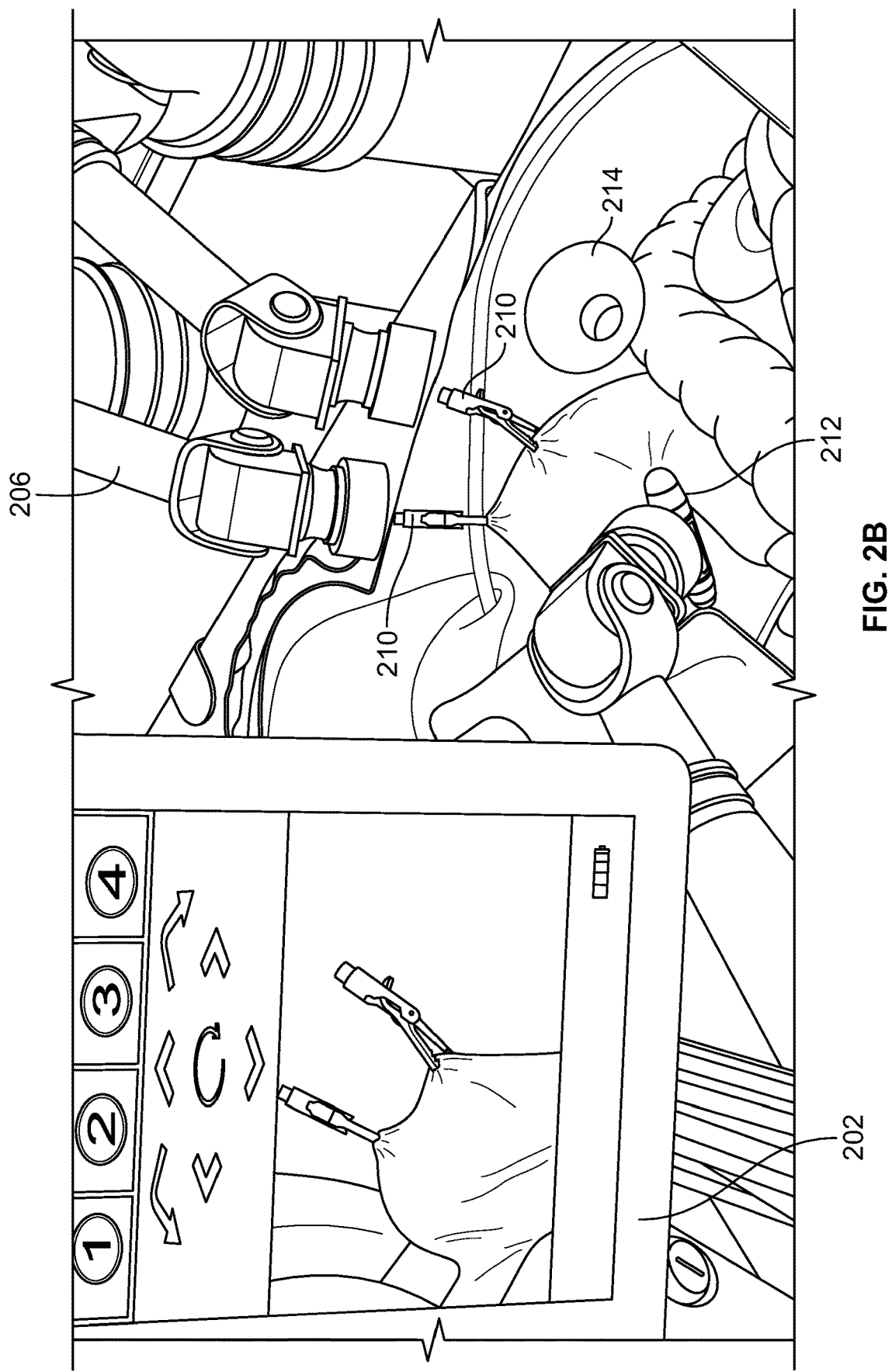

An exemplary surgical system 200 is shown in FIG. 2A. As shown there, the surgical system 200 may comprise a user interface 202 comprising a first output device (e.g., display device) and an input device (e.g., touch surface), a second output device 204 (e.g., TV display), and a plurality of support arms 206 each comprising an external magnet 208. The surgical system 200 may further comprise, as shown more clearly in FIG. 2B, a plurality of intracavity devices 210 and 212, which may be delivered via trocar 214 into a body cavity or lumen (a body cavity wall is shown transparent for ease of explanation). In other variations, the intracavity devices may be delivered via a natural orifice, such as via the mouth/esophagus/stomach or rectum. The intracavity devices 210, 212 may be configured to be attracted to respective external magnets 208. The user interface 202 may be configured to allow the operator to control the location and orientation of the intracavity devices 210, 212 through operator input to the input device for control of the position of the support arms 206 and magnetic field of the external magnet 208. Each component of the surgical system will be described in more detail herein.

Intracavity Devices

The surgical systems described herein may comprise one or more intracavity devices. These intracavity devices may be configured to be introduced into a body cavity or lumen through an access site such as a trocar or other suitable port, or through a natural orifice. The intracavity devices advanced into the body cavity or lumen through an access site may be advanced such that the intracavity device does not block the introduction and/or retrieval of other intracavity devices using the access site. Thus, a plurality of intracavity devices may be disposed and actuated within a patient body cavity or lumen.

The intracavity devices may be configured to be attracted to one or more magnets positioned externally of the body to move, reposition, and/or hold the intracavity device (which may in turn provide traction for tissue held by or otherwise in contact with the intracavity device). Accordingly, at least a portion of the intracavity devices described herein may be formed from or otherwise include one or more metallic or magnetic materials which may be attracted to a magnetic field. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. The magnetic portion of the intracavity device may thus be attracted to a magnetic field produced by an external magnetic positioning device. Furthermore, in some variations, the magnetic portion of the intracavity device may allow coupling to a delivery device, as described in more detail herein.

The intracavity devices may be used within any suitable body cavity or lumen such as but not limited to the abdominal cavity, thoracic cavity, stomach, or intestines. The intracavity devices advanced into a body cavity or lumen may perform a number of functions and are described in detail herein.

Visualization Device

In some variations, an intracavity device may comprise a visualization device configured to be attracted to one or more magnetic elements positioned externally of the body to move, reposition, and/or hold the visualization device with a desired field of view for visualization during a minimally invasive procedure.

Figure 3:
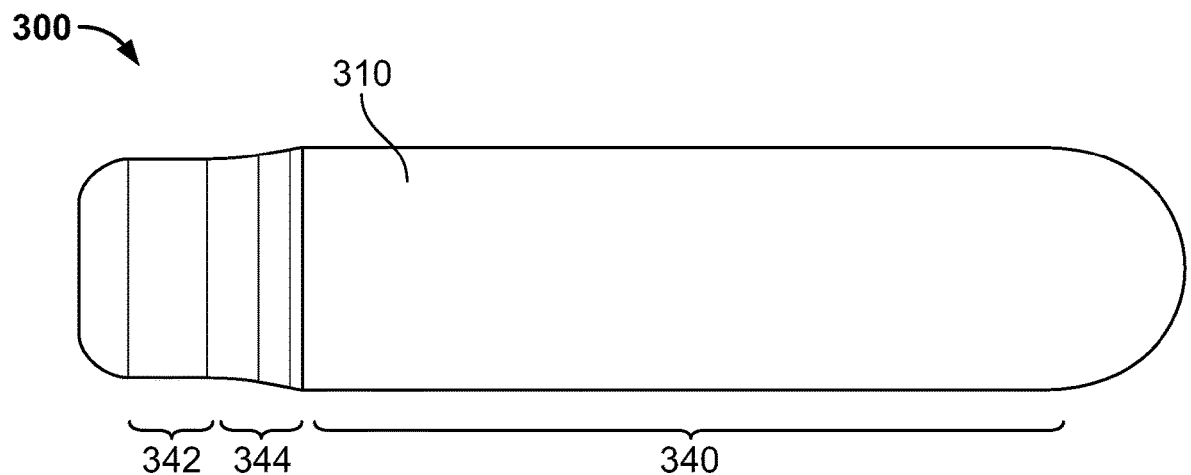
FIG. 3 depicts a side view of an illustrative variation of a visualization device.

An exemplary camera 300 is shown in FIG. 3. The camera assembly 300 may be configured to be temporarily coupled to a delivery device. The camera assembly 300 may have a capsule-like outer shape as shown, or may have any other suitable shape. The camera assembly 300 may comprise a lens and an optical sensor. The lens may be located in any suitable location, such as, but not limited to the distal end of the camera assembly 300, or along a barrel portion 310 of the camera. The camera assembly 300 may comprise one or more magnetic elements, which may be located, for example, at an end of the camera assembly 300 or along a barrel portion 310. When the camera assembly 300 is coupled to a delivery device, such as a delivery device described in more detail herein, at least a portion of the barrel portion 310 may be positioned within a distal engagement portion of the delivery device. The attractive force between a coupling magnet of the delivery device and the camera assembly 300 may hold the camera assembly 300 in place. In variations where the camera assembly 300 has a barrel portion 310 having a first segment 340 having a first outer diameter and a second segment 342 having a second outer diameter, the second outer diameter may be sized to fit within the distal engagement portion while the first outer diameter may be sized such that it is too large to fit within the distal engagement portion. In these variations, the first segment 340 (or a tapered segment 344 between the first segment 340 and the second segment 342) may act as a stop to limit the amount of the barrel portion 310 that may enter the distal engagement portion.

Figure 4:
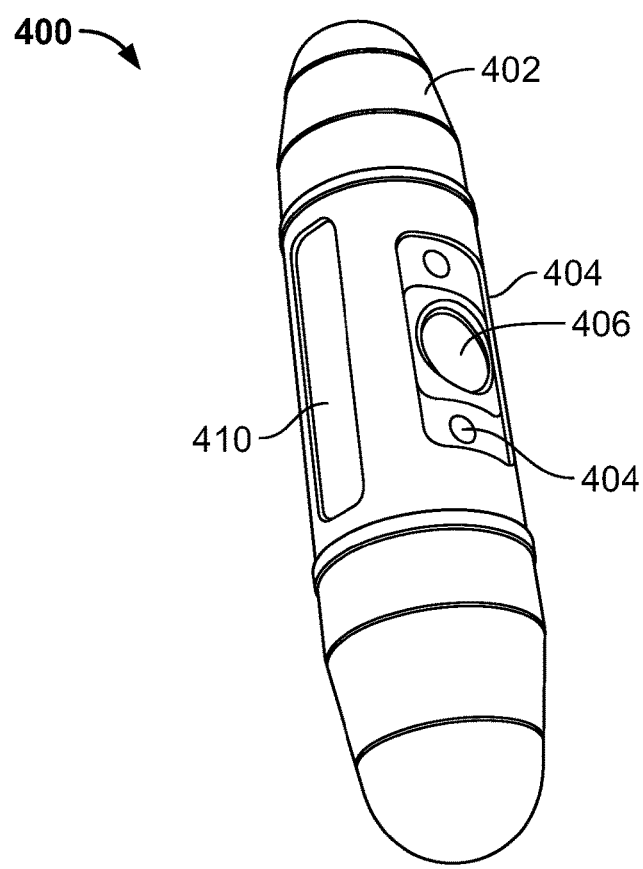
FIG. 4 depicts a perspective view of an illustrative variation of a visualization device.

FIG. 4 shows another exemplary camera assembly 400. As shown there, the camera assembly 400 comprises a camera 406 located within a capsule 402. The capsule 402 may also comprise one or more (e.g., two) light sources 404, located on either side of the camera 406. The camera 406 may comprise an optical sensor (e.g., a charged coupled device (CCD) or complementary metal-oxide semiconductor (CMOS) optical sensor). The camera assembly 400 may further comprise a magnetic portion 410 configured to be attracted to a magnetic field. In some variations, the magnetic portion 410 may comprise one or more permanent magnets and/or one or more electromagnets. Permanent magnets may be formed from suitable magnetic and ferromagnetic materials such as, but not limited to, rare-earth magnets (e.g., samarium-cobalt magnets, neodymium magnets), cobalt, gadolinium, iron, nickel, alnico alloys, ferrites, alloys thereof, combinations thereof, and the like. The magnetic portion 410 may comprise any number of individual magnets, which in some instances may be formed in an array. The magnetic portion 410 may have any suitable size and shape, such as cylindrical shape having a circular, oval, or semi-circle cross-section, a bar magnet having a rectangular or triangular cross section, a spherical magnet, or the like. In some variations, the magnetic portion 410 may comprise permanent magnets, while in other variations, the magnetic portion 410 may comprise electromagnets or electropermanent magnets. When the magnetic portion 410 comprises electromagnets or electropermanent magnets, the current may be manipulated to change the strength of the magnetic portion and/or to turn them on/off. In yet other variations, the magnetic portion 410 may comprise a ferromagnetic material that is attracted to but does not generate a magnetic field.

The magnetic portion 410 may be disposed in the camera assembly 400 such that the camera assembly 400 is asymmetrically attracted to an external magnetic field (e.g., the camera assembly 400 has one side that is more attracted to an external magnetic field). This may allow the camera assembly 400 to be oriented in a desired direction using a magnetic field such that the camera 406 may image a desired field of view. For example, the camera assembly 400 may comprise a capsule 402 comprising a magnetic portion 410 on a first side of the capsule 402 and a camera 406 disposed on a second side of the capsule 402 opposite the first side.

In some variations, the camera 406 may transition between a first and second configuration. For example, the first configuration may be a retracted position where a lens of the camera 406 is covered by the capsule 402 and a second configuration may be an extended position in which the lens of the camera 406 is exposed. In some variations, the camera 406 may be configured to pan (e.g., move side to side), tilt (e.g., move up and down), and zoom (e.g., change a focal length of a lens). Moreover, the camera assembly 400 may comprise a wired or wireless transmitter for transmitting image data including images to a controller. The camera assembly 400 may comprise a battery and/or a wire for power (e.g., power cable, power cord) for the camera 406 and/or light source 404. In some variations, the camera assembly 400 may further comprise a lens cleaning device (not shown) configured to clear obstructions such as fluid and other debris that may accumulate on an exterior of a camera lens when the camera assembly 400 is disposed in a body cavity or lumen. The lens cleaning device may comprise one or more of a wiper, sponge, fabric, hydrogel, and fluid outlets (e.g., water and/or air jets). The lens cleaning device may be actuated by the operator and/or the controller, and/or may be automated.

Grasper

In some variations, an intracavity device may comprise graspers used to grasp, retract or otherwise provide remote manipulation and/or traction to tissue. In particular, magnetically controlled graspers may be advanced into a patient and releasably engage tissue. Graspers suitable for use in the surgical systems here are described in U.S. patent application Ser. No. 14/019,370, filed Sep. 5, 2013, and titled "Grasper with Magnetically-Controlled Positioning;" U.S. patent application Ser. No. 15/195,898, filed Jun. 28, 2016, and titled "Laparoscopic Graspers and Systems Therefor;" U.S. patent application Ser. No. 13/132,185, filed Aug. 17, 2011, and titled "Remote Traction and Guidance Systems for Mini-Invasive Surgery;" and International Patent Application No. PCT/US2016/027390, filed Apr. 13, 2016, and titled "Grasper with Magnetically-Controlled Positioning," each of which is hereby incorporated by reference in its entirety.

Figure 5A:
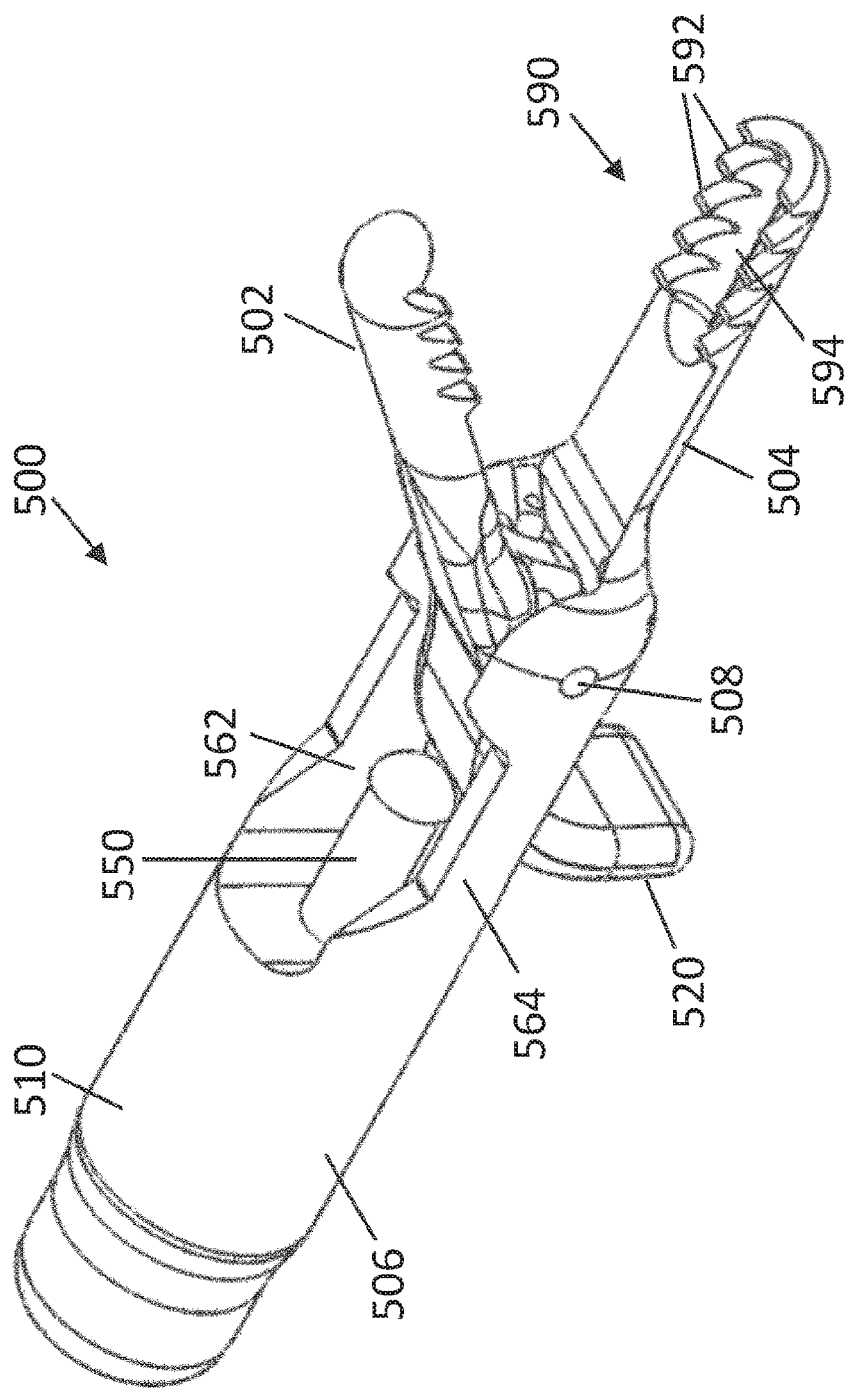

For example, FIGS. 5A-5C depict a variation of a grasper 500 suitable for use in the surgical systems described here. Specifically, FIGS. 5A and 5B show perspective and side views, respectively, of the grasper 500. As shown there, the grasper 500 may comprise a first jaw 502, a second jaw 504, and a main body 506. One or more portions of the grasper 500 may be formed from or otherwise include a magnetic or ferromagnetic material, such that it may be attracted to a magnetic field produced by an external magnetic positioning device. Generally, the first jaw 502 may be rotatably connected to the main body 506 at a pivot point 508, such that the first jaw 502 may rotate relative to the main body 506. While the second jaw 504 is shown in FIGS. 5A-5C as being fixed relative to the main body 506, it should be appreciated that in some variations the second jaw 504 may be rotatably connected to the main body 506). The first jaw 502 (and/or the second jaw 504) in variations where the second jaw 504 is rotatably connected to the main body 506) may be rotated relative to the main body 506 to actuate the grasper 500 between an open configuration and a closed configuration.

Specifically, in the open configuration, the first jaw 502 and the second jaw 504 may be held in rotationally separated positions to define a space between the first jaw 502 and the second jaw 504, as shown in FIG. 5A. In the closed configuration, the first jaw 502 and second jaw 504 may be rotationally biased toward each other, as shown in FIG. 5B. While the first jaw 502 is shown as contacting the second jaw 504 in FIG. 5B, it should be appreciated that when the grasper 500 is connected to tissue, tissue positioned between the first jaw 502 and the second jaw 504 may prevent the first jaw 502 from contacting the second jaw 504 when the grasper is in the closed configuration. The first jaw 502 and second jaw 504 may be rotationally biased toward a closed configuration in any suitable manner (e.g., via a torsional spring (not shown)).

The main body 506 of the grasper 500 may comprise a barrel portion 510 with a lumen 512 extending therethrough. A portion of a delivery device may be advanced at least partially into the lumen 512 to actuate the grasper 500 between closed and open configurations, as described in more detail herein. The outer diameter of the barrel portion 510 may be uniform, or may vary along the length of the barrel portion 510.

The first jaw 502 may be configured to rotate in any suitable manner. For example, in the variation of the grasper 500 shown in FIGS. 5A-5C, the grasper 500 may comprise a proximal arm 520 connected to the first jaw 502 such that rotation of the proximal arm 520 relative to the pivot point 508 rotates the first jaw 502 relative to the pivot point 508 (which may also rotate the first jaw 502 relative to the main body 506 and/or the second jaw 504).

Generally, at least a portion of the proximal arm 520 may be exposed relative to the main body 506, which may allow a grasping device to grasp the proximal arm 520 to rotate the first jaw 502 relative to the second jaw 504. Specifically, the main body 506 may comprise a barrel extension 560 between the barrel portion 510 and the pivot point 508. As shown in a cross-sectional side view in FIG. 5C, the barrel extension 560 may comprise a channel 562 extending at least partially through the barrel extension 560. In the variation shown in FIGS. 5A-5C, the channel 562 may extend entirely through the barrel extension 560. The barrel extension 560 may have a wall 564 on one or both sides of the channel 562. In the variation shown in FIGS. 5A-5C, the barrel extension 560 may have a wall 564 on each side of the channel 562. The proximal arm 520 may be positioned at least partially within the channel 562, and may be configured to rotate through the channel 562 as the grasper 500 is actuated between open and closed configurations.

Generally, each wall 564 of the barrel extension 560 may have a top edge 566 and a bottom edge 568. The top edge 566 and bottom edge 568 may have any suitable profile, and together may define a height of the wall 564. For example, in the variation shown in FIGS. 5A-5C, the bottom edge 568 may be linear and substantially parallel to a longitudinal axis, while the top edge 566 may include a linear portion 580 positioned between two ramped segments (labeled 582 and 584). In these variations, the height of the walls 564 may decrease along each of the ramped segments 582 and 584 toward the linear portion 580. This may facilitate grasping of the grasper 500 with a second grasping device (which may be non-magnetic) to apply forces 522 to open the jaw 502, for example, for repositioning the grasper 500 on tissue. Additionally, rib, groove, or rough surface features (not shown) may be located on the bottom edge 568 of the barrel extension 560 and/or the top surface of proximal arm 520 to increase traction or friction between the second grasping device and the grasper 500. In other variations, the top edge 566 and/or the bottom edge 568 may have a curved profile.

In some variations, the graspers described here may comprise a shuttle pin at least partially positioned in a lumen of the barrel portion of the grasper. Generally, the shuttle pin may reduce the distance an actuation rod may need to be inserted into the barrel portion in order to actuate the grasper. For example, in the variation of the grasper 500 shown in FIG. 5C, the grasper 500 may further comprise a shuttle pin 550. The shuttle pin 550 may be positioned at least partially within the lumen 512 of the barrel portion 510 of the grasper 500 and may be configured to slide relative to the lumen 512. The shuttle pin 550 may have a proximal end 552 and a distal end 554, and may assist in actuation of the grasper 500. Specifically, advancement of a portion of a delivery device (e.g., an actuation rod) into the lumen 512 of the barrel portion 510 may cause the delivery device to contact the proximal end 552 of the shuttle pin 550 and advance the shuttle pin 550 relative to the lumen 512. As the shuttle pin 550 is advanced relative to the lumen 512 of the barrel portion 510, the distal end 554 of the shuttle pin 550 may press against the proximal arm 520 (or an eccentric cam member, in variations where the grasper includes an eccentric cam member), which may cause the proximal arm 520 to act as a cam member.

Without the shuttle pin 550, an actuation rod may otherwise need to be inserted into the barrel portion 510 until it contacts the proximal arm 520 directly. When the delivery device is withdrawn relative to the shuttle pin 550, the return bias of the first jaw 502 toward a closed configuration may push the shuttle pin 550 proximally relative to the lumen 512 of the barrel portion 510.

In variations where the graspers comprise a shuttle pin, the grasper may be configured to help prevent the shuttle pin from disengaging from the grasper. In some variations, at least a portion of a shuttle pin may be configured to have an outer profile that is larger than at least a portion of the lumen of the barrel portion of a main body. For example, in the variation of the shuttle pin 550 shown in FIG. 5C, the distal end 554 may comprise a cap 556 that may have an outer diameter sized to be larger than the lumen 512 of the barrel portion 510 of the main body 506. Additionally, the grasper 500 may be configured to limit the amount of distal advancement of the shuttle pin 550.

The grasper 500 shown in FIGS. 5A-5C may be actuated in any suitable manner. In some variations, the grasper 500 may be configured such that it may be actuated by a force applied internally of the grasper 500 (e.g., via an actuation rod of a delivery device advanced through the lumen 512 of the barrel portion 510 of the grasper 500, as discussed in more detail herein), and may be further configured such that it may be actuated by a force applied externally of a grasper 500 (e.g., via a grasping device).

Retractor

In some variations, an intracavity device may comprise a retractor described used to retract or otherwise support and/or move internal organs of a patient. In particular, magnetically controlled retractors may be advanced into a patient and retract tissue to displace it from a surgical site inside the patient and/or otherwise engage tissue to increase surgical access to that tissue. Furthermore, the retractors may be configured to be maintained in position without requiring a handle or grasper.

For example, in some variations, a retractor may be configured to form a sling to retract tissue. The terminal ends may comprise a magnetic material or have magnetic masses disposed on them, such that they are configured to be attracted to a magnetic field. When a portion of the retractor is looped underneath a portion of tissue, at least a portion of the tissue may be suspended by the retractor and moved towards the patient wall. In some variations, the retractor may be configured to transition between a substantially linear configuration and the curvilinear configuration. FIGS. 6A-6B show a retractor 600 comprising a first retractor body 602 coupled to a first end of a connecting element 606 and a second retractor body 604 coupled to a second end of the connecting element 606. Generally, the retractor 600 may transition between a low-profile, substantially linear configuration and a curvilinear configuration (shown in FIGS. 6A and 6B) that may support and suspend at least a portion of tissue (e.g., an internal organ) 620 from the patient wall 630 in response to a magnetic field generated by an external magnet 640 coupled to a support arm 650. The first retractor body 602 and the second retractor body 604 may comprise beads that may generally be cuboidal, spherical, or otherwise have generally atraumatic features to decrease the likelihood of tissue damage.

Other retractors suitable for use in the surgical systems here are described in International Patent Application No. PCT/US2016/027385, filed Apr. 13, 2016, and titled "Retractor Systems, Devices, and Methods for Use," which is hereby incorporated by reference in its entirety. Other suitable retractors may include, for example, one or more of a coiled retractor, cradle retractor, lever retractor, platform retractor, and J-hook.

Additionally or alternatively, the intracavity devices are not particularly limited and may comprise one or more of a stapler, clip applier, electrocautery hook, and other surgical instrument that may be advanced in a minimally invasive manner through an access site and that is configured to be attracted to an external magnet of an external magnetic positioning device.

Delivery Device

The systems described here may in some instances comprise one or more delivery devices. The delivery devices described herein are generally configured to releasably carry one or more intracavity devices. A delivery device may be used to deliver one or more intracavity devices into a body cavity or lumen. Because the delivery devices may be releasably coupled to the intracavity devices, the delivery devices may be removed from the body cavity after delivery of the intracavity device, which may keep the access site (e.g. trocar or natural orifice) free for the delivery of other intracavity devices or other tools. In some instances, the delivery device may be configured to re-couple to the intracavity device to reposition or remove the intracavity device from a body cavity or lumen. In other instances, the system may comprise a separate retrieval device configured to reposition or remove the intracavity device from a body cavity or lumen. In some variations, the delivery device or retrieval device may be further configured to actuate an intracavity device.

When the intracavity device is a grasper, the delivery devices described here may be configured to releasably carry a grasper, and may be further configured to actuate the grasper to selectively connect the grasper to tissue or release the grasper from tissue. The delivery devices may be typically further configured to release the grasper from the delivery device (e.g., after the grasper has been connected to tissue). In some instances, the delivery device may be configured to re-couple to the grasper to reposition or remove the grasper from a body cavity or lumen. In other instances the system may comprise a separate retrieval device configured to reposition or remove the grasper from a body cavity or lumen. In some instances, the delivery device or retrieval device may be used with the grasper to remove tissue from the body. For example, the grasper may be connected to a tissue such as a gall bladder, the tissue may be severed from the body (e.g., using one or more surgical tools), and the grasper may be retrieved using the delivery device or another retrieval device to remove the grasper and tissue from the body.

Figure 10A:
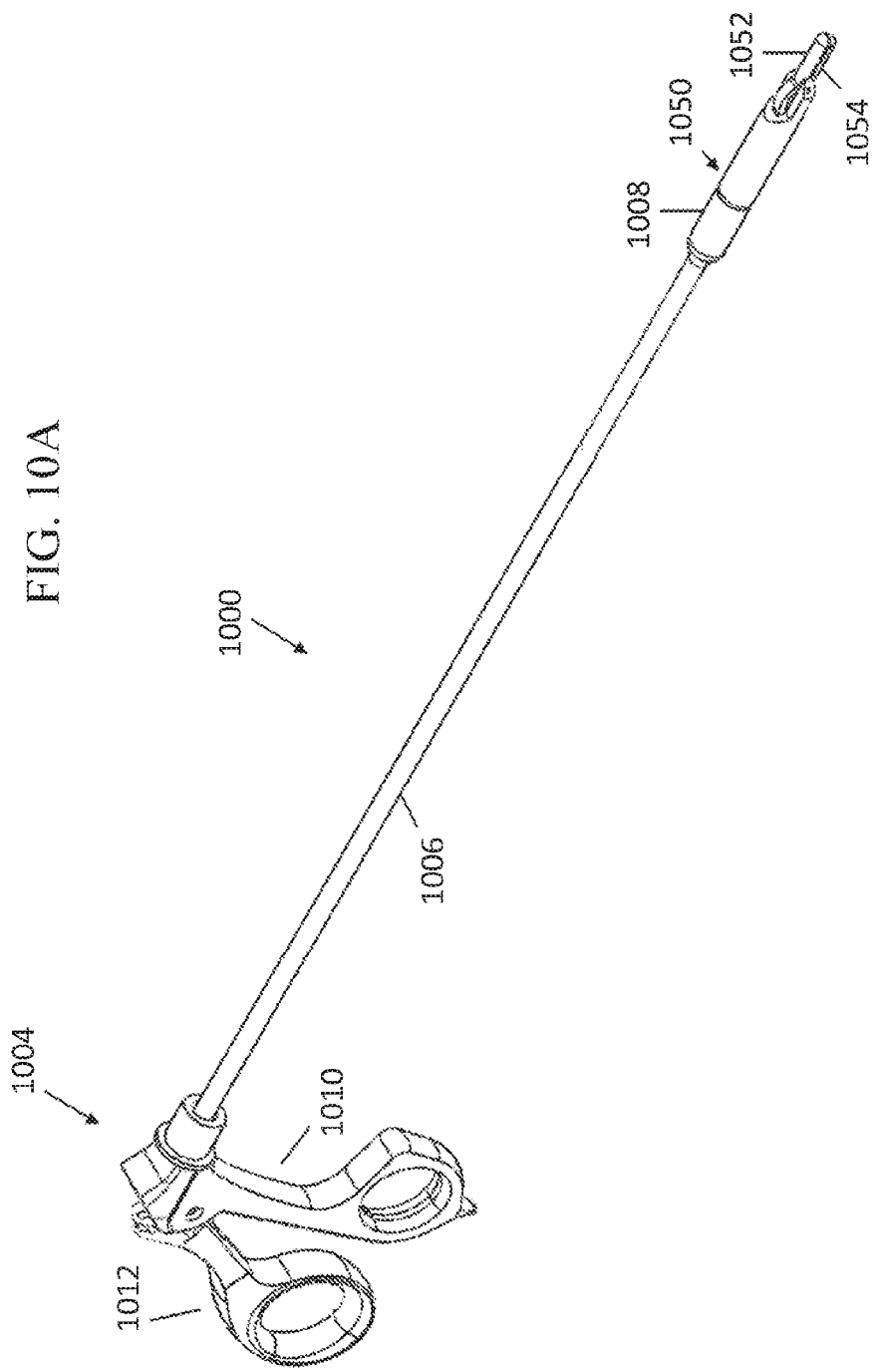
FIGS. 10A-10C depict perspective views of an illustrative variation of a delivery device used with a grasper described here.
Figure 10B:
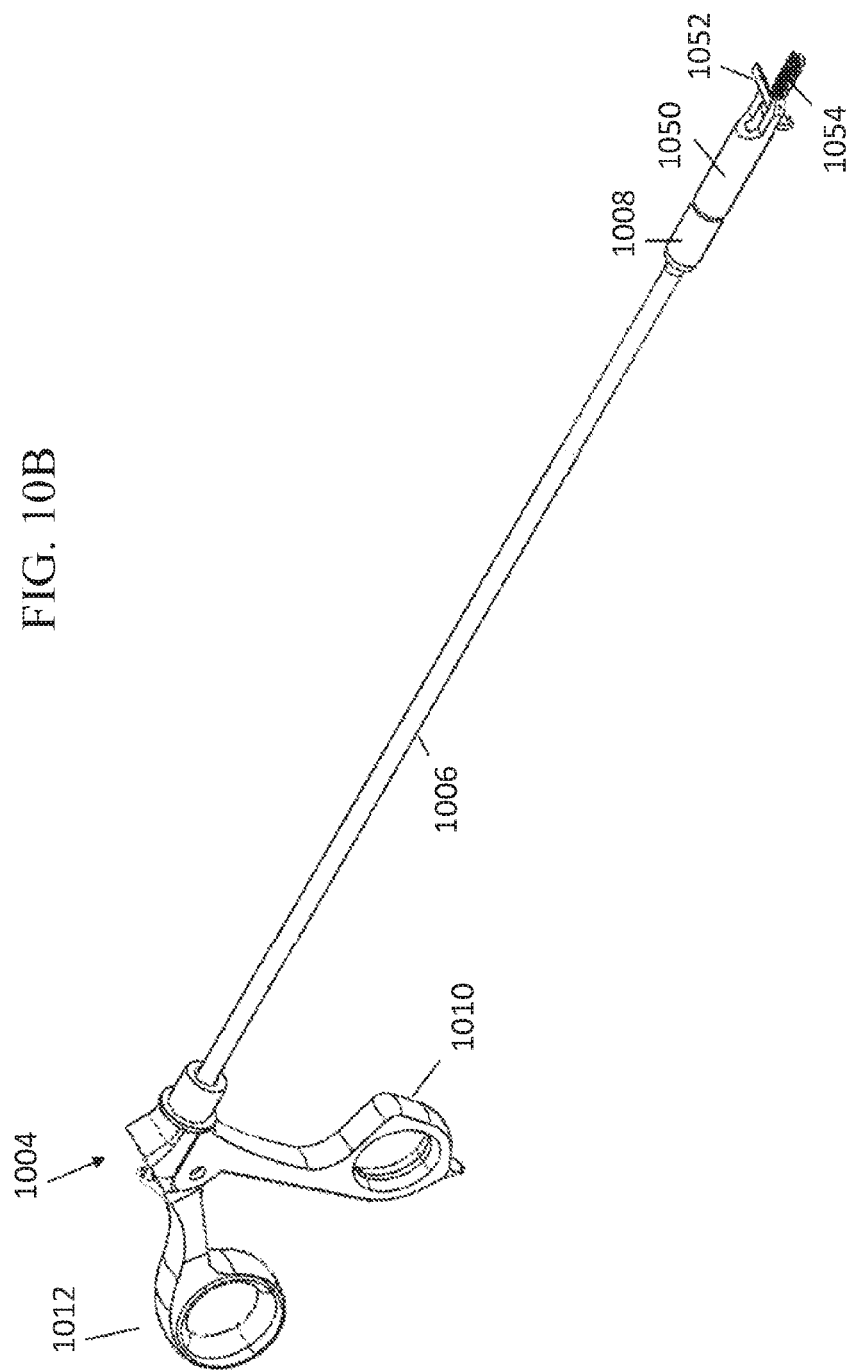
Figure 10C:
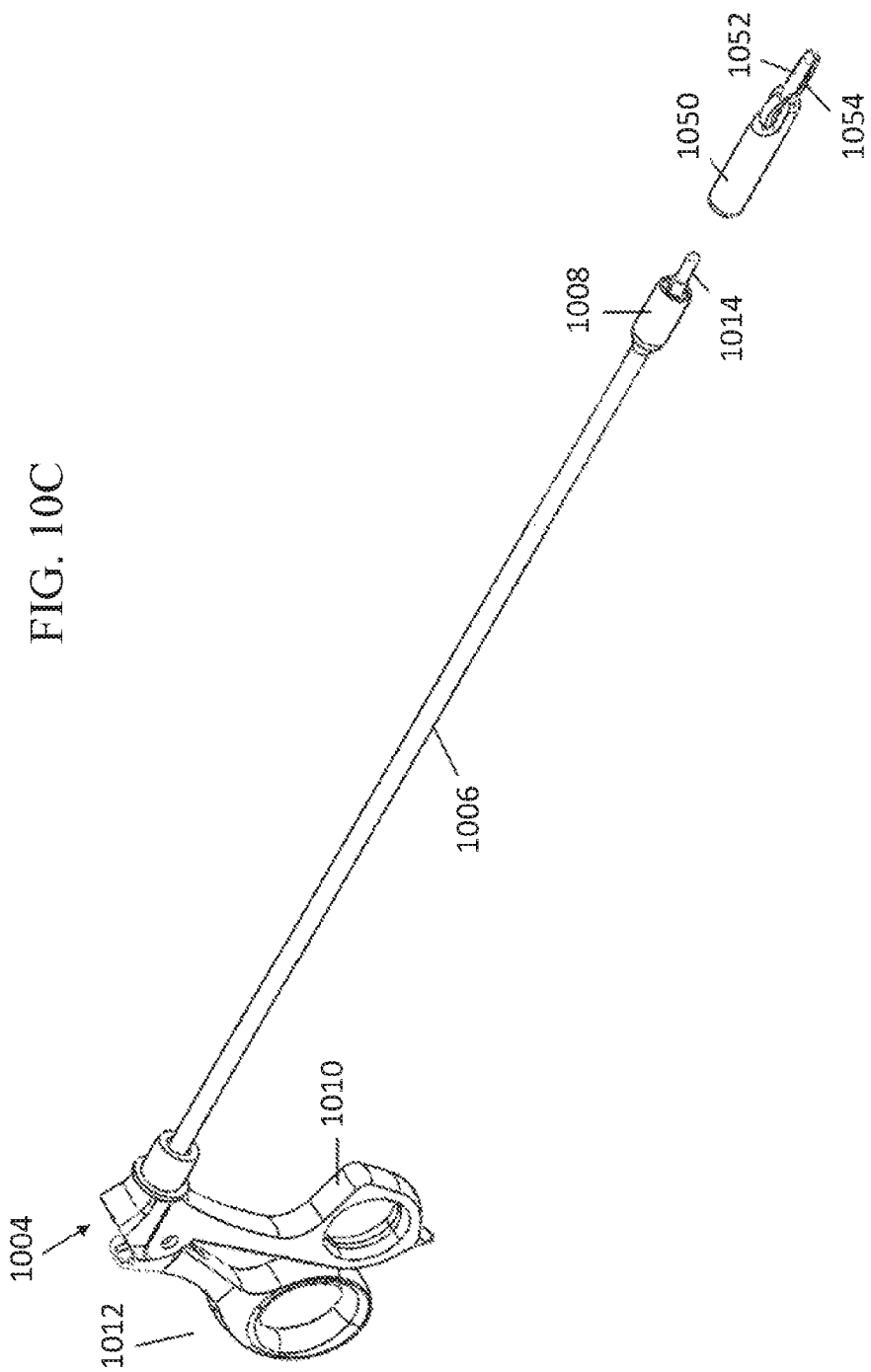

Delivery devices suitable for use in the surgical systems here are described in U.S. patent application Ser. No. 14/019,370, filed Sep. 5, 2013, and titled "Grasper with Magnetically-Controlled Positioning," which was previously incorporated by reference in its entirety. As an example, FIGS. 10A-10C depict one variation of a delivery device 1000 and a grasper 1050. The grasper may be releasably coupled to the delivery device 1000 (as shown in FIGS. 10A and 10B), and may be decoupled from the delivery device (as shown in FIG. 10C). When the grasper 1050 is coupled to the delivery device 1000, the delivery device 1000 may actuate the grasper to connect the grasper to tissue or release the grasper therefrom.

As shown in FIG. 10A, the delivery device 1000 may comprise a handle 1004, a shaft 1006 extending from the handle 1004, and a distal engagement portion 1008 at a distal end of the shaft 1006. The delivery device 1000 and grasper 1050 may be configured for laparoscopic introduction into the body. Accordingly, in some variations the grasper 1050 and delivery device 1000 may be configured for advancement through a 10 mm laparoscopic port. In these variations, the outer diameter of the grasper may be less than or equal to about 10 mm. Additionally, the delivery device 1000 may be configured such that the shaft 1006 and the distal engagement portion 1008 each have a diameter of less than or equal to about 10 mm. In some of these variations, the distal engagement portion 1008 may have an outer diameter of less than or equal to about 10 mm, while the shaft 1006 has an outer diameter of less than or equal to about 5 mm. In these variations, it may be possible to advance the distal engagement portion 1008 through a 10 mm laparoscopic port, and to further advance a second device having a diameter of about 5 mm or less through the port while the shaft 1006 is positioned in the port. It should be appreciated that shaft 1006 may have any suitable diameter (e.g., between about 1 mm and about 15 mm, between about 5 mm and about 10 mm, or the like). The shaft 1006 and distal engagement portion 1008 may be formed from any suitable materials, such as one or more medical-grade, high-strength plastics or metals, such as stainless steel, cobalt chromium, PEEK, one or more nylons, polyimide, or the like.

Generally, the handle 1004 comprises an actuation control mechanism that may be manipulated by an operator to controllably actuate the grasper. In some variations, the delivery device may comprise a separate decoupling control, which an operator may use to decouple the grasper 1050 from the delivery device 1000. In other variations, the delivery device 1000 may be configured such that an operator may use the actuation control mechanism to decouple the grasper from the delivery device in addition to actuating the grasper. For example, in the variation of the delivery device 1000 depicted in FIGS. 10A-10C, the handle 1004 of delivery device 1000 may comprise a grip portion 1010 and an actuation control mechanism comprising a trigger 1012. While shown in FIGS. 10A-10C as being a trigger 1012, it should be appreciated that the actuation control mechanism may comprise any suitable control element (e.g., a slider, a knob, or the like) capable of actuating the grasper 1050 as described in more detail herein. The trigger 1012 may be configured to both actuate the grasper 1050 and decouple the grasper 1050 from the delivery device 1000.

Specifically, in some variations the trigger 1012 may be moveable between three positions. While three distinct positions are discussed herein, it should be appreciated that the trigger 1012 may also assume one or more intermediate positions between these positions. Of the three positions, the trigger may be moveable between a first position (as shown in FIG. 10A) and a second position (as shown in FIG. 10B) to actuate the grasper 1050. Specifically, the grasper 1050 may comprise a first jaw 1052 and a second jaw 1054, and at least one of the first jaw 1052 and the second jaw 1054 may be configured to rotate relative to the grasper 1050. The grasper 1050 may be actuated between an open configuration and a closed configuration.

For example, when the trigger 1012 is in the first position (as shown in FIG. 10A), the grasper 1050 may be placed in the closed configuration. As the trigger 1012 is moved to the second position (as shown in FIG. 10B), the grasper 1050 may be moved to the open configuration. In variations where the first jaw 1052 is configured to rotate relative to the grasper 1050, moving the trigger 1012 from the first position to the second position may rotate the first jaw 1052 away from the second jaw 1054, while moving the trigger from the second position back to the first position may rotate the first jaw 1052 toward the second jaw 1054. Accordingly, by moving the trigger 1012 between the first and second positions, an operator may selectively open and close the jaws of the grasper 1050 using the delivery device 1000. To connect the grasper 1050 to tissue, an operator may place the trigger 1012 in the second position (or an intermediate position between the first and second positions) to open (or partially open) the jaws, and may manipulate the delivery device 1000 to position tissue between the first jaw 1052 and the second jaw 1054. With the tissue positioned between the jaws, the trigger 1012 may be returned to the first position to clamp the jaws against the tissue, thereby releasably connecting the grasper 1050 to the tissue.

The trigger 1012 may be configured to decouple the grasper 1050 from the delivery device. For example, the trigger 1012 may be moved from the first position (as shown in FIG. 10A) to a third position (as shown in FIG. 10C), and the delivery device 1000 may be configured to decouple from the grasper when the trigger is moved to the third position. It should be appreciated that while the actuation rod 1014 is shown extending distally from the distal engagement portion 1008 in FIG. 10C, in other variations the actuation rod may not extend distally from the distal engagement portion when the trigger is in the third position for decoupling the grasper, for example, when the grasper comprises a shuttle pin. When the same actuation control mechanism is used to actuate the grasper and decouple the grasper from the delivery device, it may be desirable to decouple the grasper from the delivery device when the grasper 1050 is in a closed configuration and engaged with tissue. Accordingly, in some variations, the first position of the trigger 1012 (which may correspond to a closed configuration of the grasper 1050) may be an intermediate position between the second position and third position. In these variations, when the trigger 1012 is placed in the second position to place the grasper 1050 in an open configuration, the trigger 1012 will move through the first position (which may move the grasper 1050 to a closed configuration) before it reaches the third position. Thus the grasper 1050 may be moved to the closed configuration before it is decoupled from the delivery device 1000.

FIGS. 11A-11D depict cross-sectional side views of a distal portion of a delivery device 1100 and a manner of actuating a grasper 1200 using the delivery device 1100. The delivery device 1100 and grasper 1200 may be configured for laparoscopic introduction into the body. Specifically, the delivery device 1100 may comprise a handle (not shown), a shaft 1106 extending from the handle, and a distal engagement portion 1108 at a distal end of the shaft 1106. The handle may comprise an actuation control mechanism that may be manipulated by an operator to controllably actuate the grasper, and may be configured as described herein with respect to the handle 1004 of the delivery device 1000 described with respect to FIGS. 10A-10C. In some of these variations, the actuation control mechanism may comprise a trigger.

Figure 11A:
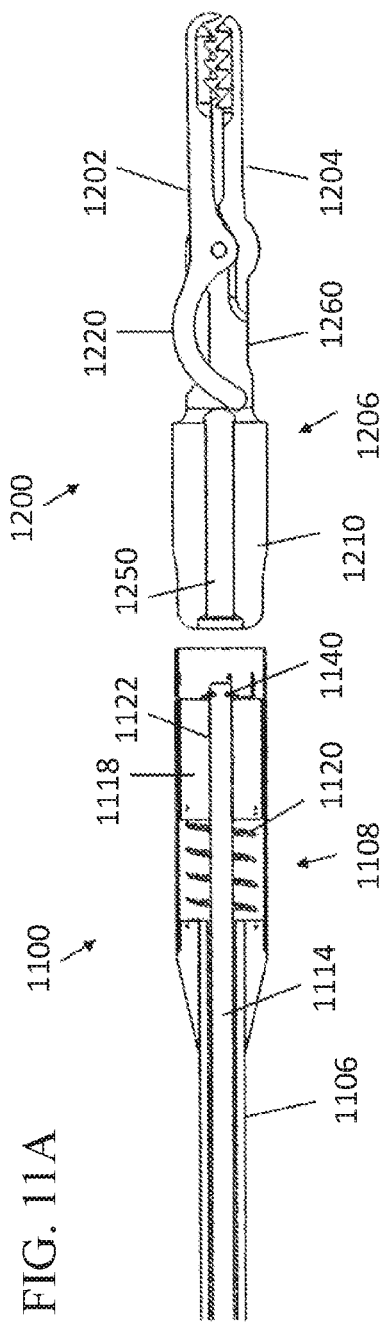
FIGS. 11A-11D depict cross-sectional side views of a distal portion of a variation of the delivery devices described here and a grasper similar to the grasper of FIGS. 5A-5C.
Figure 11B:
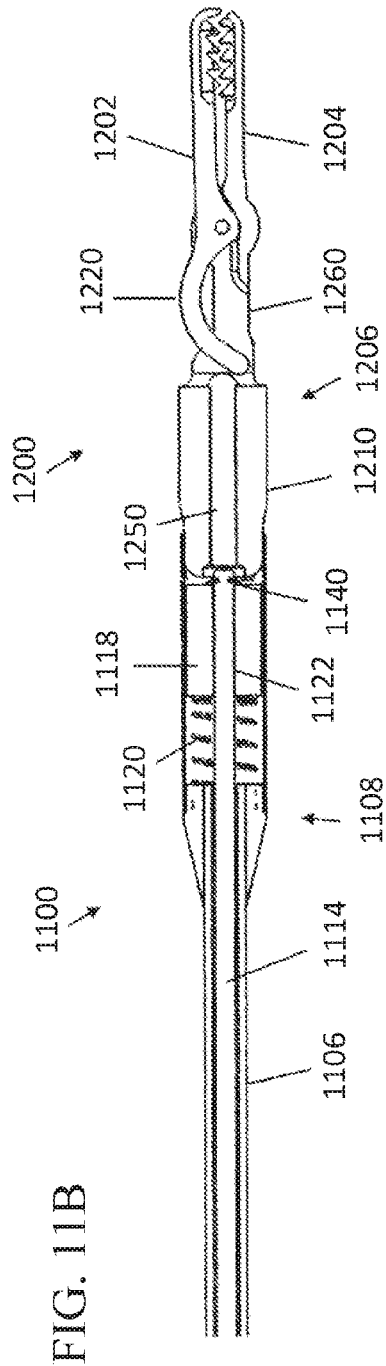
Figure 11C:
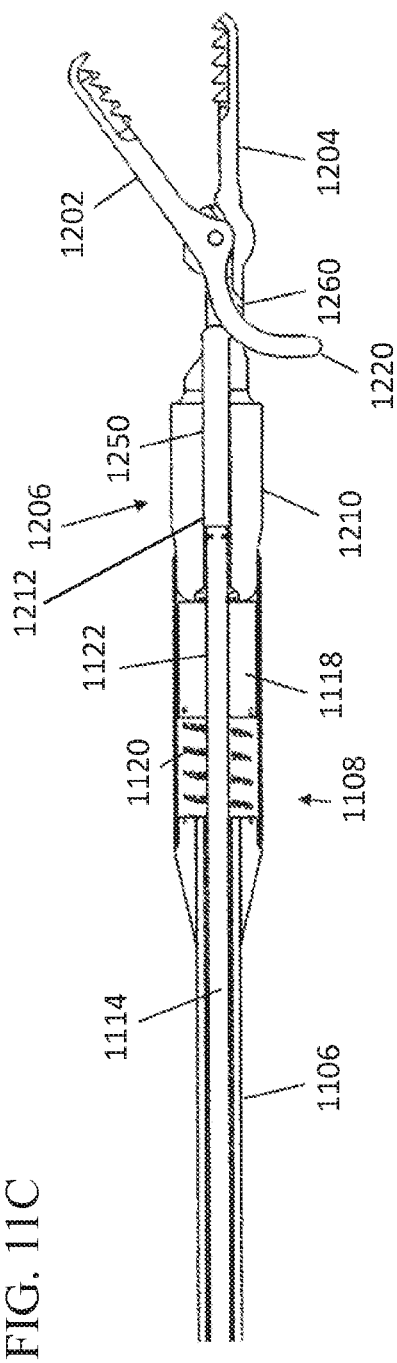

In some variations, the distal engagement portion 1108 of the delivery device 1100 may comprise a coupling magnet 1118 and a spring 1120. In these variations, the coupling magnet 1118 may be slidably housed in the distal engagement portion 1108 (e.g., in a housing of the distal engagement portion 1108). The coupling magnet 1118 may be moveable between an advanced position (as depicted in FIG. 11A-11C) and a retracted position (as depicted in FIG. 1D). The spring 1120 may be positioned within the distal engagement portion 1108 such that the spring 1120 biases the coupling magnet 1118 toward the advanced position. The delivery device 1100 may be configured to couple to the grasper 1200 when the coupling magnet 1118 is in the advanced position. At least a portion of the grasper 1200 may be formed from one or more ferromagnetic or magnetic materials. When the grasper 1200 is positioned near the distal engagement portion 1108 (such as shown in FIG.

11A), the coupling magnet 1118 may attract the grasper 1200 and temporarily couple the grasper 1200 to the delivery device 1100.

Specifically, when the grasper 1200 is temporarily coupled to the delivery device 1100, at least a portion of the barrel portion 1210 may be positioned within the distal engagement portion 1108, as shown in FIG. 11B. The attractive force between the coupling magnet 1118 and the grasper 1200 may hold the grasper 1200 in place. In variations where the grasper 1200 has a barrel portion 1210 having a first segment having a first outer diameter and a second segment having a second outer diameter, the first outer diameter may be sized to fit within the distal engagement portion 1108 while the second outer diameter may be sized such that it is too large to fit within the distal engagement portion 1108. In these variations, the second segment (or a tapered segment between the first segment and the second segment) may act as a stop to limit the amount of the barrel portion 1210 that may enter the distal engagement portion 1108.

Figure 11D:
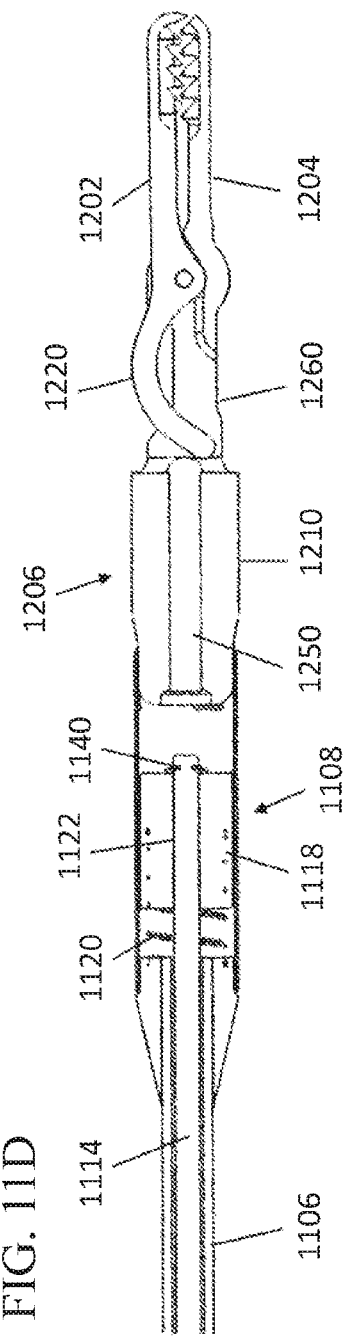

To decouple the grasper 1200 from the distal engagement portion 1108, the coupling magnet 1118 may be withdrawn to the retracted position, such as shown in FIG. 11D. As the coupling magnet 1118 is retracted, the attractive force between the coupling magnet 1118 and the grasper 1200 may pull the grasper 1200 proximally relative to the distal engagement portion 1108. The second segment (or the tapered segment) may limit the withdrawal of the grasper 1200, such that the distance between the coupling magnet 1118 and the grasper 1200 increases. This may decrease the attractive force between the coupling magnet 1118 and the grasper 1200, which may allow the grasper 1200 to be pulled from, released from, or otherwise fall from the distal engagement portion 1108.

The coupling magnet 1118 may be retracted in any suitable manner. For example, in the variation of the delivery device 1100 shown in FIGS. 11A-11D, the delivery device 1100 may comprise an actuation rod 1114 slidably disposed in the shaft 1106. The actuation rod 1114 may be configured to retract the coupling magnet 1118. For example, the actuation rod 1114 may be slidably disposed within a lumen 1122 of the coupling magnet 1118. In some variations, at least a segment of the actuation rod 1114 may be sized and configured such that the portion of the actuation rod 1114 cannot fully pass through the lumen 1122. For example, the variation shown in FIGS. 11A-11D, a segment 1140 of the actuation rod may have a diameter greater than a diameter of the lumen 1122. Since the segment 1140 cannot fully pass through the lumen 1122 of the coupling magnet 1118, further withdrawal in the proximal direction of the actuation rod 1114 may cause the segment of the actuation rod 1114 to pull on and withdraw the coupling magnet 1118. When the actuation rod 1114 is subsequently advanced, the spring 1120 may advance the coupling magnet 1118 with the actuation rod 1114 until the coupling magnet 1118 reaches the advanced position.

The actuation rod 1114 may be advanced or retracted relative to the shaft 1106 to actuate and/or release the grasper 1200. In variations where the handle comprises a trigger, the trigger may be operatively connected to the actuation rod 1114, such that movement of the trigger slides the actuation rod 1114. Movement of the actuation rod 1114 may rotate the first jaw 1202 of the grasper 1200. Specifically, when the grasper 1200 is coupled to the delivery device 1100 (as shown in FIG. 11B), the actuation rod 1114 may be aligned with the lumen 1212 of the barrel portion 1210 such that the actuation rod 1114 enters the lumen 1212. As the actuation rod 1114 is advanced into the lumen 1212, the actuation rod 1114 may press against the proximal end 1252 of the shuttle pin 1250 and advance the shuttle pin 1250 along the lumen 1212. As the shuttle pin 1250 is advanced along the lumen 1212, the distal end of the shuttle pin 1250 may move into a channel of the barrel extension 1260. The distal end of the shuttle pin 1250 may in turn push against the proximal arm 1220 (e.g., against a portion of the proximal arm 1220 that is positioned in the channel 1262 and aligned with the lumen 1212). The proximal arm 1220 may act as a cam to convert the linear motion of the shuttle pin 1250 into rotation of the proximal arm 1220, which may in turn rotate the first jaw 1202 away from the second jaw 1204. When the first jaw 1202 is spring-biased toward the second jaw 1204, the rotation of the proximal arm 1220 may overcome this spring bias, which may allow the actuation rod 1114 to hold the first jaw 1202 in its open position, as shown in FIG. 11C.

Additionally, the first jaw 1202 may rotate back toward the second jaw 1204 when the actuation rod 1114 is retracted. Specifically, as the actuation rod 1114 is withdrawn, the return bias of the first jaw 1202 may cause the proximal arm 1220 to push against the shuttle pin 1250, which may slide the shuttle pin 1250 proximally within the lumen 1212. This may return the grasper to a closed configuration, such as shown in FIG. 11B. When the grasper 1200 is closed around tissue, the actuation rod 1114 may be further retracted to release the grasper 1200 from the delivery device 1100. When a trigger is moveable between three positions to actuate and release the grasper 1200, placing the trigger in the first position may position the actuation rod 1114 in a position as illustrated in FIG. 11B, in which the grasper 1200 may be coupled to the delivery device 1100 in a closed configuration. Moving the trigger to the second position may advance the actuation rod to the position illustrated in FIG. 11C, in which the grasper 1200 may be releasably coupled to the delivery device 1100 in an open configuration. Moving the trigger to the third position may retract the actuation rod 1114 to the position illustrated in FIG. 11D, in which the grasper 1200 may be decoupled from the delivery device 1100.

It should be appreciated that while delivery devices are described herein primarily with reference to use with a grasper, the delivery devices described herein may also be used to reversibly couple to another intracavity device to deliver, position and reposition, and/or remove another intracavity device. For example, in some instances the delivery devices may be used to deliver, position and reposition, and/or remove a visualization device, such as a camera and/or light source.

Magnetic Positioning Device

The surgical systems described herein may comprise one or more external magnetic positioning devices comprising an external magnet, support arm, and/or sensors. The external magnets may generate a magnetic field configured to attract one or more intracavity devices. By controlling the position and/or strength of the external magnets and thereby the position and/or strength of the magnetic fields, the external magnets may control the position of the intracavity devices disposed within a body cavity or lumen of a patient. This may free space at an access site (e.g., port) of the patient to allow additional intracavity devices to be advanced into the patient and reduce, if not eliminate, the need for a second operator such as a skilled surgeon.

External Magnets

The external magnets may be configured to generate a magnetic field, such that when the external magnet is positioned near a patient, a magnetic field may be generated inside the patient. This magnetic field may apply a force to and manipulate an intracavity device. In some variations, the external magnet may comprise one or more permanent magnets, one or more electromagnets, and/or one or more electropermanent magnets. Permanent magnets may be formed from suitable magnetic and ferromagnetic materials such as, but not limited to, rare-earth magnets (e.g., samarium-cobalt magnets, neodymium magnets), cobalt, gadolinium, iron, nickel, alnico alloys, ferrites, alloys thereof, combinations thereof, and the like. The external magnets may comprise any number of individual magnets, which in some instances may be formed in an array. The external magnets may have any suitable size and shape, such as cylindrical shape having a circular, oval, or semi-circle cross-section, a bar magnet having a rectangular or triangular cross section, a spherical magnet, or the like. In some variations, the external magnets may comprise permanent magnets, while in other variations, the external magnets may comprise electromagnets or electropermanent magnets. When the external magnets comprise electromagnets or electropermanent magnets, the current may be manipulated to change the strength of the external magnets and/or to turn them on/off. For example, an increase in the magnetic field generated by the external magnet may bring an intracavity device in contact with a body cavity wall of a patient while a decrease in the magnetic field may reposition the intracavity device away from the body cavity wall. Additionally, a stronger magnetic field may be needed to magnetically couple the intracavity device with the external magnet through a thick body cavity wall (e.g., a thick abdominal wall), whereas a weaker magnetic field may be desirable to reduce the attractive force between the intracavity device and the external magnet through a thin body cavity wall (e.g., a thin abdominal wall).

Support Arms

The surgical systems described herein may comprise one or more support arms. Generally, each external magnet may be fixed relative to a support arm where the support arm may be configured to moveably suspend the external magnet so to move and hold the magnet at a desired location. With the external magnet suspended or held at a desired location by the support arm, an operator and/or controller may move the external magnet externally of a patient. The support arm may be, for example, an articulated robotic arm, SCARA robotic arm, and/or linear robotic arm. The support arm may comprise one or more segments coupled together by a joint (e.g., shoulder, elbow, wrist). Joints are mechanisms that provide a single translational or rotational degrees of freedom. For example, the support arm may have six degrees of freedom. The set of Cartesian degrees of freedom may be represented by three translational (position) variables (e.g., surge, heave, sway) and by the three rotational (orientation) variables (e.g., roll, pitch, yaw). Of course, other variations of the support arm may have less than six degrees of freedom. The support arm may be configured to move over all areas of a patient body in up to three dimensions and may also maintain the external magnet at an orientation perpendicular to a surface of the patient. The support arm may comprise one or more motors configured to translate and/or rotate the joints and move the support arm to a desired location and orientation. In some variations, the position of the support arm may be temporarily locked to fix the position of the external magnet. The support arm may be mounted to any suitable object, such as furniture (e.g., a bed rail), a wall, a medical cart, a ceiling, or may be self-standing. Additionally or alternatively, the support arm may be configured to be moved manually. The support arm may be configured to carry a payload comprising the support arm, external magnet), intracavity device magnetically coupled to the external magnet, and any tissue coupled to the intracavity device (e.g., a gallbladder held by a grasper). In some variations, each support arm may move a respective intracavity device.

When an external magnetic positioning device is magnetically coupled to an intracavity device, movement of the external magnet via movement of the support arm may in turn move the intracavity device disposed within a body cavity or lumen of the patient. For example, coronal movement of the external magnet relative to the patient may result in a corresponding coronal movement of the intracavity device. As another example, moving the external magnet closer to the intracavity device using the support arm may increase the attraction between the external magnet and the intracavity device so as to bring the intracavity device in contact with a patient cavity wall, while moving the external magnet further away from the intracavity device may reduce the magnetic attraction and reposition the intracavity device away from the body cavity wall. Thus, by controlling the strength of the external magnet and position of the external magnet using the support arm, and thereby the strength and position of the magnetic field, the magnetic positioning device may control the position of the intracavity devices disposed within a body cavity or lumen of a patient. In some variations, a strength and/or position of the external magnet may be used to control a force of a magnetically coupled intracavity device against a body cavity wall or lumen wall using the sensors described in detail herein.

Sensors

The external magnetic positioning devices may optionally comprise one or more sensors to determine a location of a portion of one or more external magnetic positioning devices (e.g., support arms, external magnets), patient body surfaces (e.g., internal cavity wall, breasts), and surgical system components (e.g., intracavity devices, trocar, control console). For example, an external magnetic positioning device may comprise one or more sensors configured to detect a location of a patient body surface and calculate a proximity of the magnetic positioning device relative to the patient such that the controller may ensure that the support arm and/or the external magnet do not contact the patient. For example, each segment of a support arm may comprise an inductive proximity sensor to calculate a distance between the support arms. As another example, an infrared, radar, or ultrasonic range finder mounted on the support arm and/or external arm may be configured to calculate a distance to the patient. As yet another example, the magnetic positioning device may comprise optical sensors internal and/or external to the support arms configured to visualize the other support arms, operator, input/output device, patient platform, patient, or the like. A controller may be configured to maintain a predetermined distance between the magnetic positioning device and a patient body surface such as a distance of about 1 mm, about 5 mm, or about 10 mm. The one or more sensors may be further configured to detect a proximity of the magnetic positioning device relative to other magnetic positioning devices and system components to prevent contact with each other or the patient. A controller may be configured to maintain a predetermined distance between the magnetic positioning device and a patient body surface such as a distance of about 1 mm, about 5 mm, or about 10 mm. Thus, a controller may limit a range of motion of the support arm.

As another example, a magnetic field and/or position of an external magnet may be controlled using a force sensor of the external magnetic positioning device and/or intracavity device, such as for an intracavity device in contact with an internal body cavity wall. A contact force of the intracavity device and/or external magnet with the body cavity wall may be reduced if a force sensor detects that the force exceeds a predetermined threshold. The sensors may comprise one or more of a force sensor (e.g., Hall sensor, load cell, springs), proximity sensor, optical sensor, motion sensor, accelerometer, gyroscope, laser rangefinder, radar, and LIDAR.

Controller

A surgical system 100, as depicted in FIG. 1, may comprise a controller 110 in communication with a plurality of support arms 120 and/or intracavity devices 130. The controller 110 may comprise one or more processors 112 and one or more machine-readable memories 114 in communication with the one or more processors 112. The controller 110 may be connected to the support arms 120 and/or intracavity devices 130 by wired or wireless communication channels. The controller 110 may be located in the same or different room as the patient. In some variations, the controller 110 may be coupled to a patient platform or disposed on a medical cart adjacent to the patient and/or operator. The controller 110 may be configured to control one or more components of the system 100, such as intracavity devices 130 that may visualize a body cavity or lumen, grasp tissue, retract tissue, hold and/or drive a needle, and the like. In some variations, the controller 110 may be configured to coordinate movement and orientation of intracavity devices 130 within a body cavity or lumen through corresponding movement and control of the support arms 120 and external magnets 122.

The controller 110 may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

Processor

The processor 112 may incorporate data received from memory 114 and operator input to control a plurality of support arms 120, external magnets 122, intracavity devices 130, and/or delivery devices 132. The memory 114 may further store instructions to cause the processor 112 to execute modules, processes and/or functions associated with the system 100. The processor 112 may be any suitable processing device configured to run and/or execute a set of instructions or code and may comprise one or more data processors, image processors, graphics processing units, physics processing units, digital signal processors, and/or central processing units. The processor 112 may be, for example, a general purpose processor, a Field Programmable Gate Array (FPGA), an Application Specific Integrated Circuit (ASIC), configured to execute application processes and/or other modules, processes and/or functions associated with the system and/or a network associated therewith. The underlying device technologies may be provided in a variety of component types such as metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

Memory

Some variations of memory 114 described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as air or a cable). The media and computer code (also may be referred to as code or algorithm) may be those designed and constructed for a specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical discs; solid state storage devices such as a solid state drive (SSD) and a solid state hybrid drive (SSHD); carrier wave signal processing modules; and hardware devices that are specially configured to store and execute program code such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Network Interface

As depicted in FIG. 1, surgical systems 100 described herein may communicate with networks 160 and computer systems 164 through a network interface 116. In some variations, the surgical system 100 may be in communication with other devices via one or more wired and/or wireless networks. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some variations, the network interface 116 may comprise a radiofrequency receiver, transmitter, and/or optical (e.g., infrared) receiver and transmitter. The network interface 116 may communicate by wires and/or wirelessly with one or more of the support arm 120, external magnet 122, sensor 124, intracavity device 130, delivery device 132, input device 140, output device 150, network 160, database 162, and server 164.

User Interface

User interface 118 may serve as a communication interface between an operator and the system 100. The user interface 118 may comprise an input device and output device (e.g., touch screen and display) and be configured to receive input data and output data from one or more of the support arm 120, external magnet 122, sensor 124, intracavity device 130, delivery device 132, input device 140, output device 150, network 160, database 162, and server 164. For example, images generated by an intracavity device 130 comprising a visualization device may be received by user interface 118, processed by processor 112 and memory 114, and displayed by the output device 150 (e.g., monitor display). Sensor data from one or more sensors 124 may be received by user interface 118 and output visually, audibly, and/or through haptic feedback by one or more output devices 150. As another example, operator control of an input device 140 (e.g., joystick, keyboard, touch screen) may be received by user interface 118 and then processed by processor 112 and memory 114 for user interface 118 to output a control signal to one or more support arms 120, external magnets 122, intracavity devices 130, and delivery devices 132.

Input Device

Figure 7:
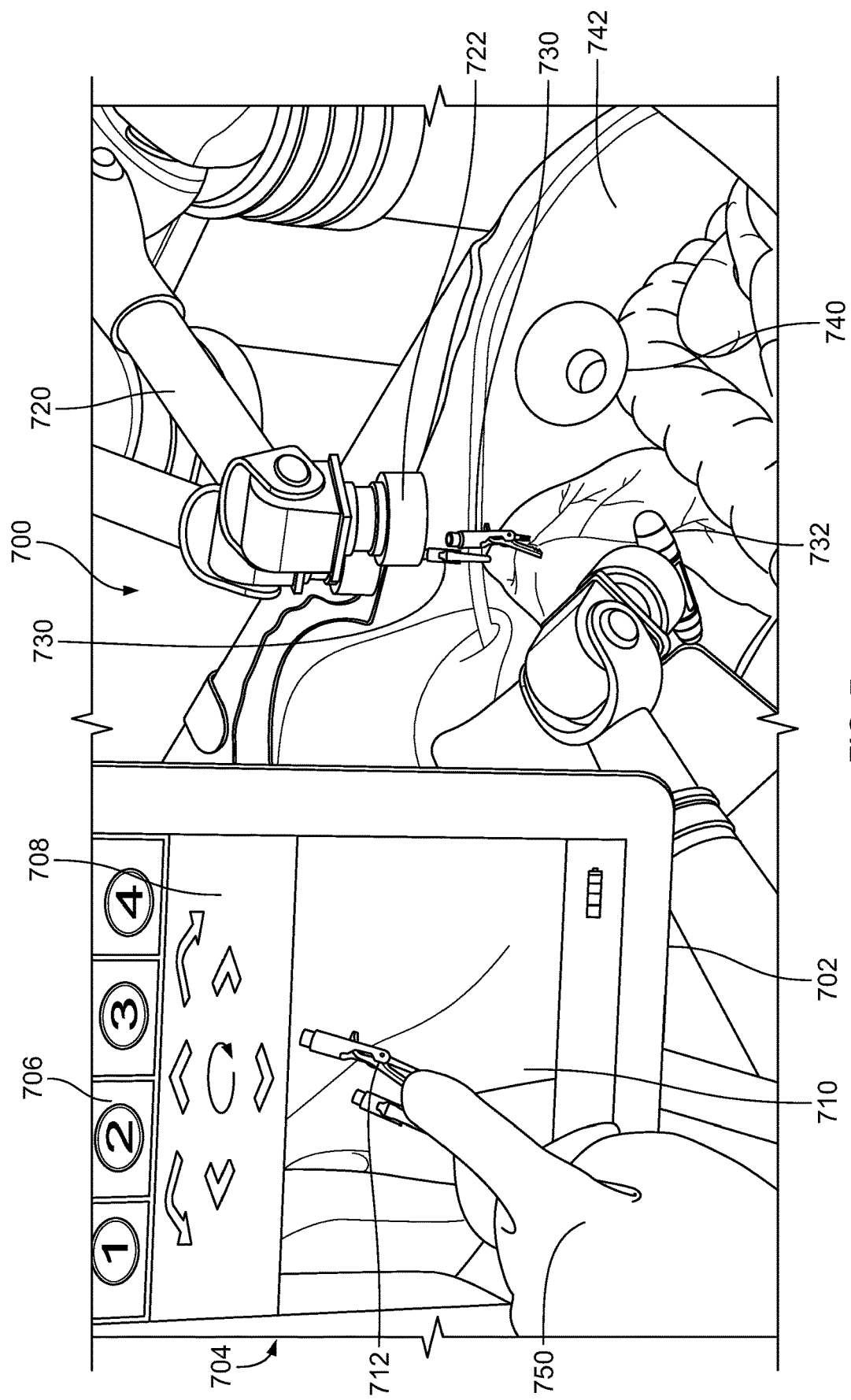
FIG. 7 depicts a perspective view of an illustrative variation of a user interface of a surgical system.

In some variations, a single operator may control one or more components of a surgical system 100 using one or more input devices 140. Some variations of an input device may comprise at least one switch configured to generate a control signal. The input device may be coupled to a patient platform and/or disposed on a medical cart adjacent to the patient and/or operator. However, the input device may be mounted to any suitable object, such as furniture (e.g., a bed rail), a wall, a ceiling, or may be self-standing. The control signal may include, for example, a movement signal, activation signal, magnetic field strength signal, and other signals. In some variations, the input device may comprise a wired and/or wireless transmitter configured to transmit a control signal to a wired and/or wireless receiver of a controller. A movement signal (e.g., for the control of movement, position, and orientation) may control movement in at least four degrees of freedom of motion, and may include yaw and/or pitch rotation. For example, as depicted in FIG. 7, an input/output device 702 (e.g., user interface device) may comprise a touch surface for an operator 750 to provide input (e.g., finger contact to the touch surface) corresponding to a movement signal to move an external magnetic positioning device 720 and intracavity device 730 within the body cavity or lumen. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. The exemplary input control scheme depicted in FIG. 7 is discussed in further detail herein.

In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal. In variations of a system comprising a plurality of input devices, different input devices may generate different types of signals. For example, some input devices (e.g., button, analog stick, directional pad, and keyboard) may be configured to generate a movement signal while other input devices (e.g., step switch, rocker switch) may be configured to transition a component of the surgical system (e.g., support arm, sensor, intracavity device) between a first configuration and second configuration (e.g., on and off, extended and retracted, open and closed).

In some variations, a single input device may be configured to control a plurality of system components (e.g., intracavity devices, support arms). For example, a touch surface of an input/output device 702 may be configured to control a plurality of external magnetic positioning devices 720 and/or intracavity devices 712 through a set of device selector buttons 706 and device control buttons 708, as discussed in further detail herein.

In other variations, a plurality of input devices may be configured to control a single component of the surgical system (e.g., intracavity device) to enhance operator flexibility. For example, an operator may choose to control a support arm using combinations of a joystick, directional pad, soft keys, voice commands, and the like.

In still other variations, each input device of a surgical system may be associated with a corresponding component of the surgical system. Some non-limiting examples include: a joystick may be configured to control movement of a support arm; a touch screen may be configured to pan, tilt, and/or zoom a visualization device; a jog dial may be configured to control the jaw positions of a grasper; and a step switch may be configured to release a delivery device from an intracavity device.

In variations of the input device comprising one or more buttons, button presses of varying duration may execute different functions. For example, a lumen output level of a light source may be configured to increase with a longer button press. Conversely, a shorter duration button press may correspond to a different function such as deactivating the light source.

In some variations, a surgical system may comprise a plurality of input devices provided in separate housings, where for example a first input device may be handheld and/or portable while a second input device may be stationary. In some variations, a first input device may comprise a tablet including a touch screen display and a second input device may comprise a step switch or foot pedal. The step switch may in some variations be a safety switch that must be engaged at the same time as contact with the touch screen before a control signal is transmitted to the surgical system. Output of a control signal upon simultaneous engagement of a first input device and second input device may confirm that operator input to the first input device is intentional.

Output Device

An output device 150 of a surgical system 100 may output sensor data corresponding to a patient and/or surgical system, and may comprise one or more of a display device, audio device, and haptic device. The output device may be coupled to a patient platform and/or disposed on a medical cart adjacent to the patient and/or operator. In other variations, the output device may be mounted to any suitable object, such as furniture (e.g., a bed rail), a wall, a ceiling, and may be self-standing.

A display device may allow an operator to view images of one or more intracavity devices, support arms, external magnets, body cavities, and tissue. For example, an intracavity device comprising a visualization device (e.g., camera, optical sensor) located in a body cavity or lumen of a patient may be configured to image an internal view of the body cavity or lumen and/or other intracavity devices. An external visualization device may be configured to image an external view of the patient and one or more external magnetic positioning devices. Accordingly, the display device may output one or both of internal and external images of the patient and system components. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

An audio device may audibly output patient data, sensor data, system data, alarms and/or warnings. For example, the audio device may output an audible warning when monitored patient data (e.g., blood pressure) falls outside a predetermined range or when a malfunction in a support arm is detected. As another example, audio may be output when operator input is overridden by the surgical system to prevent potential harm to the patient and/or surgical system (e.g., collision of support arms with each other, excessive force of the intracavity device against a patient cavity wall). In some variations, an audio device may comprise at least one of a speaker, piezoelectric audio device, magnetostrictive speaker, and/or digital speaker. In some variations, an operator may communicate to other users using the audio device and a communication channel. For example, the operator may form an audio communication channel (e.g., VoIP call) with a remote operator and/or observer.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). Haptic feedback may in some variations simulate a resistance encountered by an intracavity device within a body cavity or lumen (e.g., magnetic field and tissue resistance). Additionally or alternatively, haptic feedback may notify that an operator input is overridden by the surgical system to prevent potential harm to the patient and/or system (e.g., collision of support arms with each other). Operator interaction with a user interface utilizing an input and output device is discussed in more detail herein.

User Interface

FIG. 7 depicts an illustrative variation of surgical system 700 comprising an input/output (I/O) device 702 (e.g., user interface device comprising a touch surface and display), a plurality of external magnetic positioning devices 720 (e.g., support arms and external magnets) magnetically coupled to respective intracavity devices 730, 732 (grasper and camera assembly, such as described herein). The intracavity devices 730, 732 may be advanced into a patient body cavity 742 (having a transparent cavity wall for ease of explanation) through a port 740 (e.g., trocar). In other variations, the intracavity devices may be delivered via a natural orifice, such as via the mouth/esophagus/stomach or rectum. The input/output device 702 may comprise a graphical user interface (GUI) 704 configured to output patient data, system data, and sensor data from any internal and/or external sensor of the surgical system 700. For example, I/O device 702 may be configured to display internal, real-time images 710 generated by a camera assembly 732 located within the body cavity 742. The GUI 704 may allow an operator to control (e.g., operate and move) a plurality of intracavity devices 730, 732 magnetically coupled to respective external magnetic positioning devices 720 using a single input scheme. The GUI 704 may display an image generated by, for example, an intracavity camera assembly, external camera, and/or stored images (e.g., computed tomography or magnetic resonance images). The operator 750 may select an image source for display on the GUI 704. The GUI 704 may comprise text such as a time, date, system status, patient data, and other data. The text may be displayed over an image of the GUI 704 such as the internal image 710.

In some variations, the GUI 704 may display a plurality of soft keys for device selection and control. The device selector buttons 706 in FIG. 7 may comprise one or more of a number, color, name, shape, and image identifying one or more intracavity devices for selection. In some variations, a device selector button 706 may select multiple devices within a group according to device characteristics such as function and type. For example, selection of button "2" in FIG. 7 may select for active control each of the graspers 730. Active control refers to control of a selected device through input of one or more device control buttons (e.g., device control buttons 708). A subsequent selection of button "2" may deselect the graspers 730 from active control. In some of these variations, selection of a group of intracavity devices 730, 732 may prompt display of a sub-menu (not shown) for selection of a subset of intracavity devices within the initially selected group. Moreover, an operator 750 may select a plurality of device groups for control through selection of a plurality of device selector buttons 706. This may allow, for example, a set of graspers and camera assemblies to move and/or operate together within a body cavity or lumen.

Additionally or alternatively, an operator 750 may select an intracavity device 730 for control using a real-time internal image 710 generated by camera assembly 732. A controller may process the internal image 710 (e.g., using an image processing unit of a processor) to classify the intracavity devices 730 within the internal image 710 as an imaged intracavity device 712. A device selector button 706 may be defined by an outline of the imaged intracavity device 712. Operator 750 may contact the imaged intracavity device 712 displayed on the I/O device 702 as a device selector button for a predetermined duration to select the intracavity device 730 for active control.

In some variations, an operator 750 may select a plurality of intracavity devices 730, 732 for simultaneous control by selection of corresponding device selection buttons 706. It may be useful in some variations to select a group of intracavity devices 730, 732 for simultaneous device control. For example, concurrent selection and control of a group of graspers 730 grasping the same organ 744 may allow coordinated operation and movement. Movement of a single grasper 730 while another grasper 730 coupled to the same tissue is stationary may cause damage (e.g., tearing) to the grasped organ 744. Additionally or alternatively, an operator 750 may select an intracavity device 730, 732 for device control through a voice command. An audio device may output an audio confirmation of the selected intracavity device 730, 732.

It should be appreciated that selection of a particular intracavity device 730, 732 for control using device control buttons 708 may also select for control of the external magnetic positioning device 720 magnetically coupled to the intracavity device 730, 732. This is because some control functions of the intracavity device 730, 732, such as movement through the body cavity, may be effected through movement and control of a magnetically coupled external magnetic positioning device 720. Other functions of the intracavity device 730, 732 (e.g., activation of a light source) may not require control of the external magnetic positioning device 720.

The device control buttons 708 in FIG. 7 may comprise one or more of a number, color, name, shape, and image identifying a control function to be executed by the selected device. In some variations, a device control button 708 may execute the same function among multiple devices 730, 732. For example, selection of button ">" (right arrow) in FIG. 7 may command the support arms 720 to move each of the graspers 730 to the right relative to a predetermined coordinate system (e.g., based on a reference frame defined by the image or patient anatomical planes). The GUI 704 may simultaneously display device control buttons 708 for a plurality of devices (e.g., camera pan/zoom control buttons and grasper movement control buttons). This may allow an operator 750 to input control signals to maintain the grasper 730 in view of the camera assembly 732 as the grasper 730 moves.

In some variations, an imaged intracavity device 712 may function as a device control button 708 to move and/or control the selected intracavity device 730. For example, an operator 750 may contact the imaged intracavity device 712 and perform a "drag and drop" touch input of sliding their finger across the I/O device 702 and releasing contact with the I/O device 702 to input a movement signal of the intracavity device 730 to the GUI 704. In some variations, a stored image or real-time image of the intracavity device 730 may move across the GUI 704 with the operator input. This drag and drop input may move the intracavity device 730 along a two-dimensional plane while depthwise movement along a perpendicular third axis may be input via a device control button 708. Other button press combinations may execute other functions of the intracavity device 730. For example, a double tap of the imaged intracavity device 712 may transition the grasper 730 between a first configuration (e.g., open jaws) and second configuration (e.g., closed jaws).

An intracavity device movement signal input to GUI 704 may be processed by a controller to move a support arm 720 and/or modify an external magnet 722 field strength. In some variations, a change in magnetic field strength may move the intracavity device along the transverse plane of the patient. For example, a decrease in magnetic field strength may move the intracavity device deeper into a body cavity and away from the support arm 720. In other variations, input of a movement signal of the intracavity device 730 along a coronal plane of the patient may correspond with parallel movement of the support arm 720.

Additionally or alternatively, an operator 750 may audibly control an intracavity device 730, 732 through voice commands. For example, operator 750 may effectuate control and movement of an intracavity device 730, 732 using predetermined phrases (e.g., "turn on light", "open jaws of grasper", "pan camera 10 degrees", "advance 5 centimeters"). An audio device may optionally output an audio confirmation of the command.

In some variations, the I/O device 702 may comprise a single housing (as shown in FIG. 7) or may comprise separate housings for an input device (e.g., joystick) and an output device (e.g., display).

Sterile Coverings

The surgical systems described herein may comprise one or more sterile coverings configured to create a sterile barrier around portions of the surgical system. In some variations, the surgical system may comprise one or more sterile coverings to form a sterile field. For example, a sterile covering may be placed between the positioning devices and the patient, forming a barrier between an interior, non-sterile side including the patient and intracavity devices and an exterior, sterile side including the operator, support arm, and external magnet. Additionally or alternatively, components of the system may be sterilizable. The sterile covering may, for example, comprise a sterile drape configured to cover at least a portion of a system component.

For example, a sterile covering (e.g., sterile bag) may be configured to create a sterile barrier with respect to an external magnet of a magnetic positioning device. The sterile bag may be clear and allow an operator to visualize and manually manipulate a position of the external magnet by, for example, an operator grabbing a handle of a support arm or a handle attached to an external magnet through the sterile bag. The sterile covering may conform tightly around one or more system components or may drape loosely so as to allow components to be adjusted within the sterile field (e.g., adjustment of mechanical bolts of a support arm).

II. Methods

Also described here are methods for treating a patient using the surgical systems described herein. A single operator may operate a surgical system comprising a plurality of intracavity devices without requiring assistance from another operator to operate the surgical system. Generally, the methods described here comprise advancing one or more of intracavity devices into a body cavity or lumen of a patient, non-invasively coupling the intracavity devices to corresponding external magnetic positioning devices, controlling the intracavity devices, moving the intracavity devices within the body cavity or lumen through control of the corresponding external magnetic positioning devices, and actuating the intracavity devices. The operator may thus control a surgical system comprising the intracavity device(s) from a single control console. Because multiple components of the surgical system may be controllable via a single control console and may not require active control (e.g., an intracavity device may be held in place via magnetic force, such that an operator or other person need not hold the intracavity device in place), the methods described here may allow a single operator to perform a surgical procedure, even when that surgical procedure involves a number of tools. This may have numerous benefits, such as reducing the cost of surgery.

Figure 8:
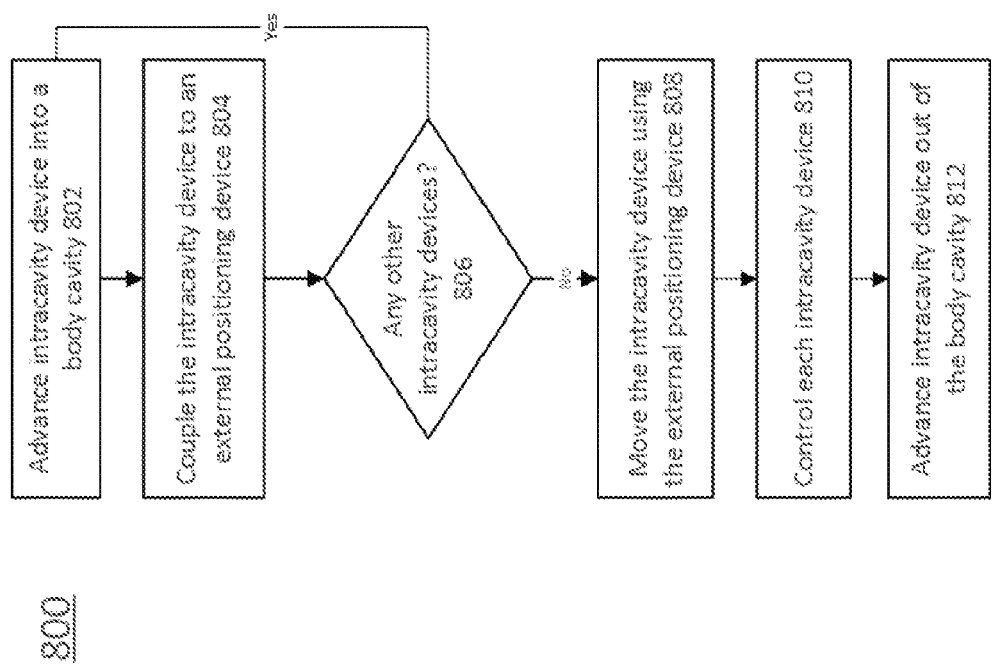
FIG. 8 depicts a flowchart representation of an illustrative variation of a surgery process.
Figure 9A:
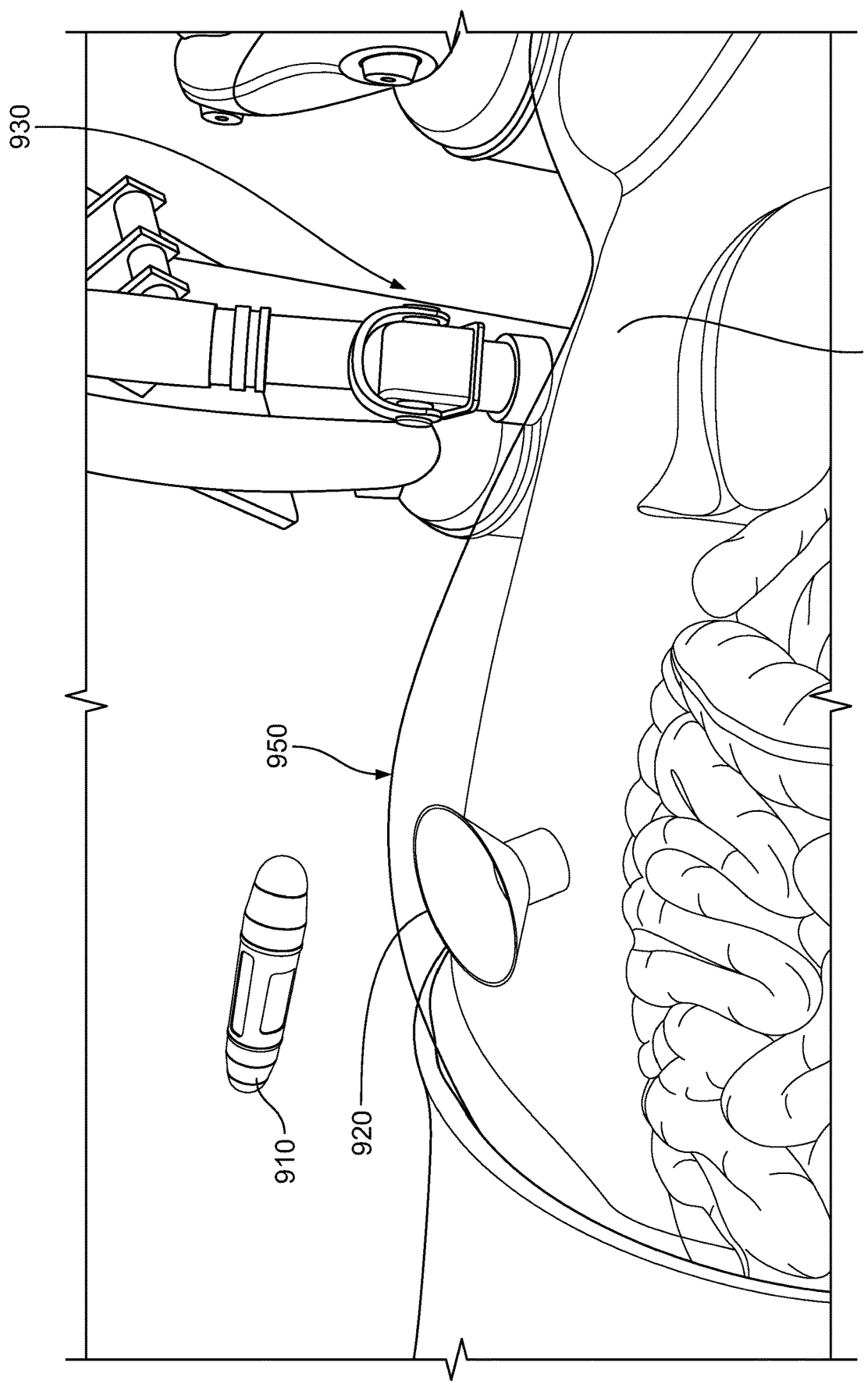
FIGS. 9A-9E depict perspective views of an illustrative variation of the surgery process depicted in FIG. 8.
Figure 9B:
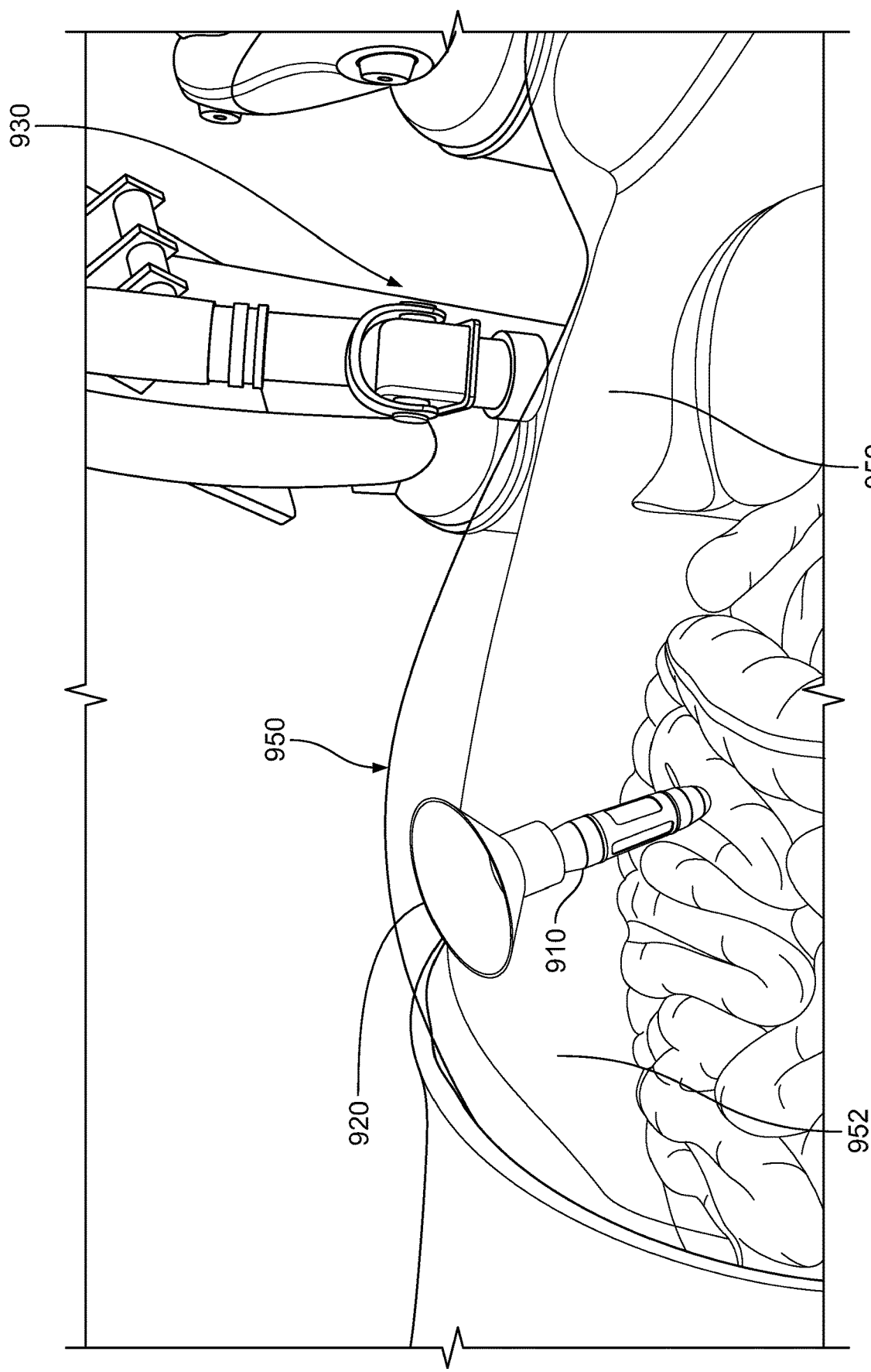

FIG. 8 is a flowchart 800 of an illustrative method of performing minimally invasive surgery. The method 800 may begin with advancement of an intracavity device into a body cavity through an access site 802. As shown in FIG. 9A, an intracavity device 910 is initially disposed externally of the patient 950. The intracavity device 910 may be advanced through a port 920 disposed in an access site of a patient 950. FIG. 9B illustrates the intracavity device 910 advanced through the port 920 and disposed in a body cavity 952 (a body cavity wall is shown transparent for ease of explanation) of the patient 950. The body cavity is not particularly limited and may be, for example, an abdominal cavity or thoracic cavity. In other variations, the intracavity device may be advanced into a body lumen. The port 920 may be, for example, a trocar disposed within a patient cavity wall, but in other variations the intracavity device may be delivered via a natural orifice. The intracavity device 910 may have a size and configuration for advancement through the port 920. In some variations, the intracavity device 910 may be advanced through the port 920 using a delivery device (such as those described herein) releasably coupled to the intracavity device 910 (not shown). It should be appreciated that because the intracavity device 910 is advanced through the port 920 and then subsequently coupled to an external magnetic positioning device 930 via a magnetic force, the pathway remains available for other intracavity devices to be advanced into the body cavity 952.

Figure 9C:
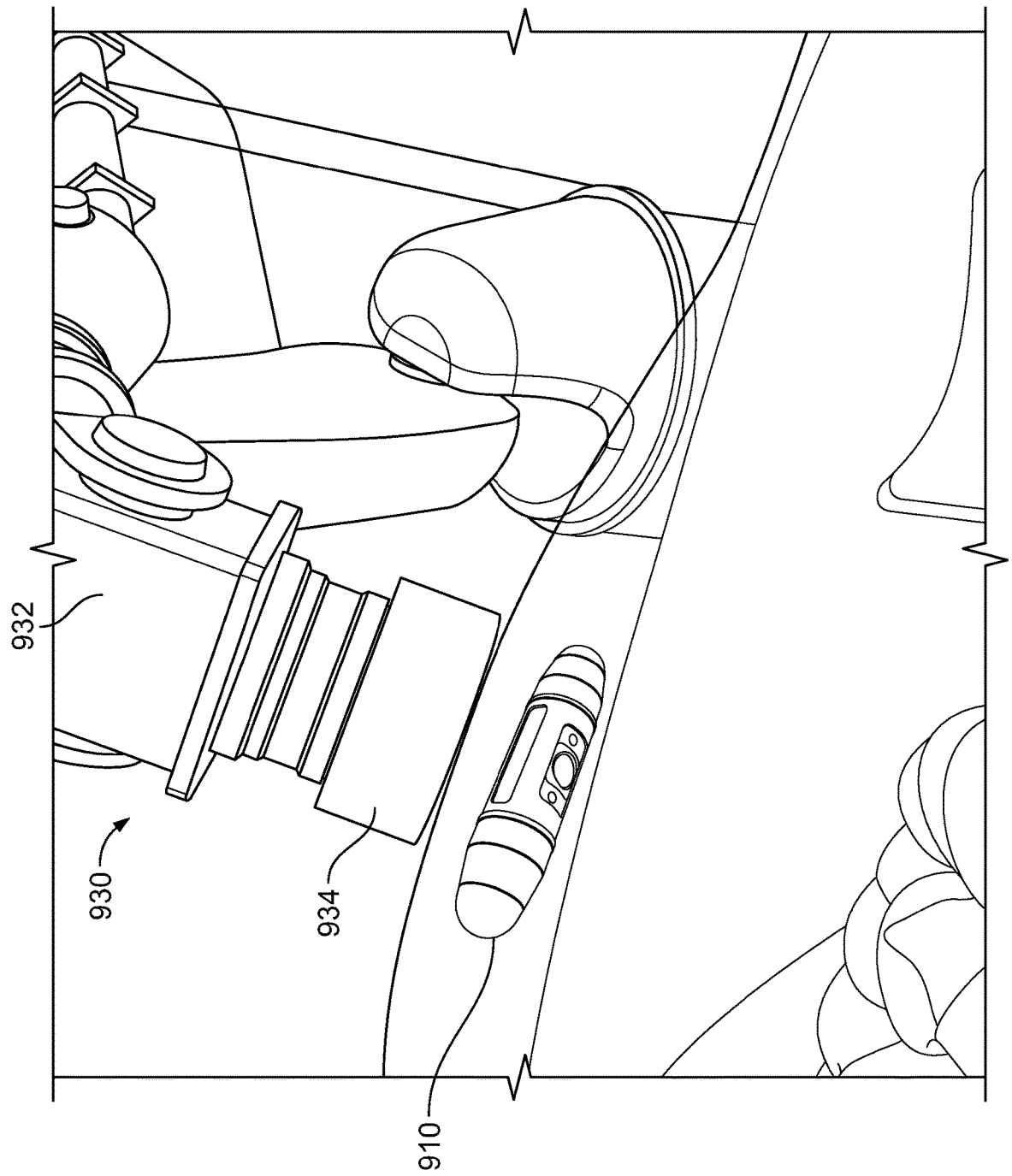

The intracavity device disposed within a body cavity or lumen may be coupled to an external magnetic positioning device through the patient cavity wall 804. As shown in FIG. 9C, the intracavity device 910 comprising a magnetic portion may be magnetically coupled to an external magnetic positioning device 930 comprising a support arm 932 and an external magnet 934. For example, the external magnet 934 may generate a magnetic field to attract the intracavity device 910 towards the body cavity wall and external magnetic positioning device 930. This magnetic coupling may hold the intracavity device 910 relative to the external magnetic positioning device 930 with the patient cavity wall disposed therebetween. A determination may be performed of whether any other intracavity devices are to be advanced into the body cavity 806. If so, steps 802, 804, and 806 may be repeated.

Repositioning of the external magnetic positioning device 930 through movement of the support arm 932 may move the external magnet 934 and in turn move the coupled intracavity device 910 within the body cavity 952. For example, lateral movement of the external magnet 934 may move the coupled intracavity device 910 laterally, while movement of the external magnet 934 toward or away from the patient cavity wall may increase or decrease, respectively, a force of the intracavity device 910 against the patient cavity wall. A change in the magnetic field strength of the external magnet 934 (e.g., through a change in applied current to the external magnet 934 when the external magnet is an electromagnet or electropermanent magnet) may modify the position of the intracavity device 910 relative to the external magnetic positioning device 930. For example, increasing the magnetic field strength of the external magnet 934 may draw the intracavity device 910 closer towards a patient cavity wall and the external magnet 934 and/or increase a contact force of the intracavity device 910 against the patient cavity wall. Conversely, decreasing the magnetic field strength of the external magnet 934 may increase the distance between the intracavity device 910 and the patient cavity wall and/or decrease a contact force of the intracavity device 910 against the patient cavity wall. In some variations of surgical systems described herein, each of a plurality of intracavity devices may be magnetically coupled to a corresponding external magnetic positioning device, thereby allowing independent control of each intracavity device within a body cavity or lumen.

In some variations, prior to the external magnet magnetically coupling to the intracavity device, the support arm may position the external magnet at a predetermined position external to the patient. For example, the external magnet may be positioned directly above an opening of the port, which allows the intracavity device to be magnetically coupled to the external magnetic positioning device as the intracavity device is introduced into the body cavity or lumen. In other variations, the intracavity device may be positioned relative to the external magnetic positioning device using a delivery device coupled to the intracavity device. The delivery device may, for example, release the intracavity device once the intracavity device is magnetically coupled to the external magnetic positioning device.

Figure 9D:
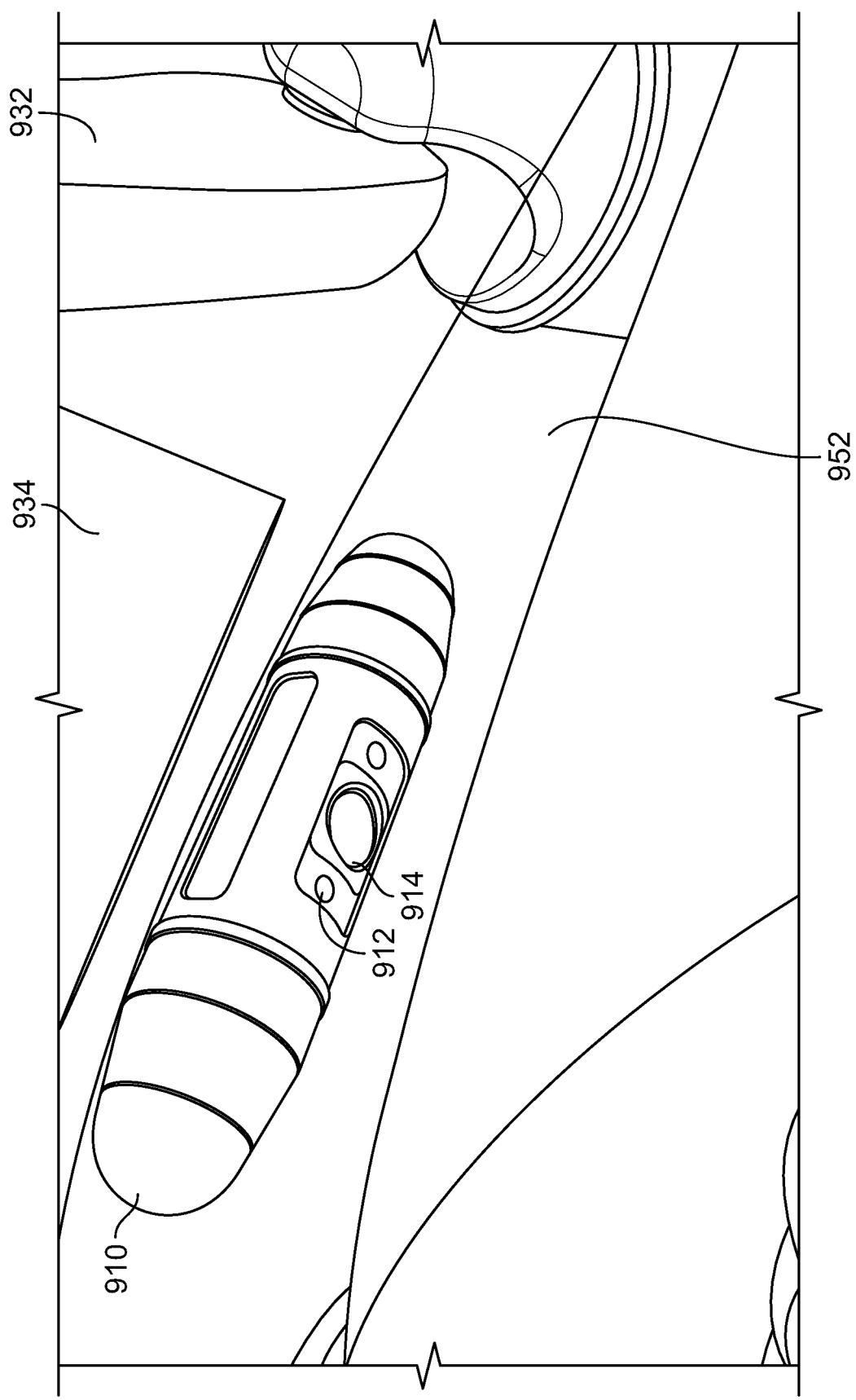
Figure 9E:
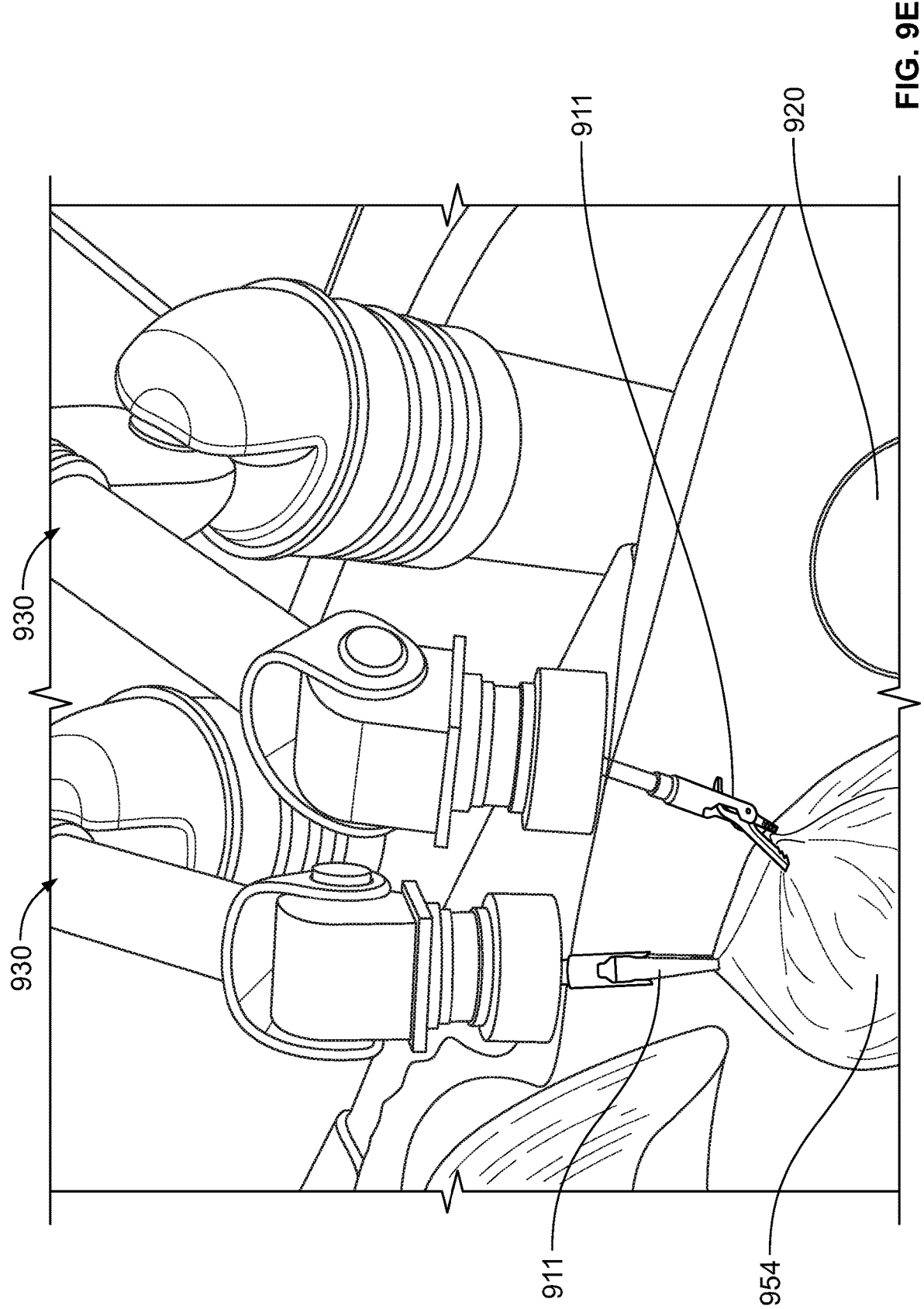

The intracavity device magnetically coupled to the external magnetic positioning device may be moved to a desired location and orientation using the external magnetic positioning device 808. A single operator may control each intracavity device using one or more input devices. Different intracavity devices may be moved to different locations within a body cavity or lumen. For example, FIGS. 9C-9D show an intracavity device 910 (e.g., a visualization device comprising a camera assembly) located near or in contact with a patient cavity wall in an orientation where an optical sensor may image one or more other intracavity devices and tissue (e.g., organs). FIG. 9E shows a pair of graspers 911 grasping tissue 954. In response to a movement signal input by an operator, one or more of the magnetic field strength of an external magnet and location of a support arm may be modified to change a position and/or orientation of the graspers 911. In some variations, an operator may view internal images of the patient displayed on a display device as the operator inputs a control signal (e.g., FIG. 7). The operator may further control each intracavity device individually or in groups. Of course, the operator may manually control an intracavity device (e.g., using a delivery device as described herein) in conjunction with control of the surgical system.

In variations where one or more of the intracavity devices and external magnets contact the patient cavity wall, a contact force of the intracavity device and/or external magnet with the patient cavity wall may be reduced to reduce potential harm to patient tissue when force sensors detect that the force exceeds a predetermined threshold. For example, a magnetic field strength of the external magnet may be reduced in response to force exceeding about 10 N.

An operator may input a control signal using a GUI to control each intracavity device in the body cavity or lumen 810. The functions performed by each intracavity device will of course depend on the intracavity device. As shown in FIG. 9D for example, a light source 912 of intracavity device 910 may be activated to illuminate a body cavity 952 and an optical sensor 914 may generate images of the body cavity 952. In some variations, the optical sensor 914 may further pan (e.g., move side to side), tilt (e.g., move up and down), zoom (e.g., change the magnification of the lens system), and focus (e.g., change a focal length of a lens). Some visualization devices may comprise a lens wiping device for cleaning the lens. Other intracavity devices may manipulate tissue. For example, the graspers 911 in FIG. 9E are shown in a closed configuration where tissue 954 is grasped between the jaws of the grasper 911. In other variations, a retractor may be configured to transition between a low profile configuration and a curvilinear configuration. Other non-limiting examples of intracavity device control include: a delivery/retrieval device configured to releasably carry one or more intracavity devices; an electrocautery hook configured to cauterize tissue; a suction device configured to suction fluid and/or tissue in the body cavity or lumen; a stapler configured to staple tissue.

Furthermore, one or more internal and/or external sensors may be configured to be controlled by an operator such as a proximity sensor, force sensor, magnetic field sensor. For example, a force sensor may be disposed on a side of the intracavity device that is more attracted to an external magnetic field (e.g., on a side opposite the light source 912 and optical sensor 914). In some variations, the intracavity device 910 may comprise a wireless transmitter (not shown) for transmitting sensor data (e.g., force sensor data) to a controller. When an external magnetic field is generated in the patient body cavity and the intracavity device 910 is attracted towards the patient cavity wall and makes contact with the patient cavity wall, the force sensor may transmit force sensor data to the controller using the wireless transmitter of the intracavity device 910. The wireless transmitter of the intracavity device 910 may further transmit image data generated by the optical sensor 914. In other variations, an external magnetic positioning device 930 may comprise a wired or wireless transmitter for transmitting sensor data (e.g., force sensor data, proximity data) to a controller. In some of these variations, an external force sensor may be disposed on a side of the external magnet 934 opposite the support arm 932. When the external magnet 934 and external force sensor are in contact with a patient body surface, the external force sensor may transmit external force data to the controller using the transmitter of the external magnetic positioning device 930.

An operator may input a control signal using a GUI to advance each intracavity device out of the body cavity or lumen 812. For example, the external magnetic positioning device may move the support arms and/or modify a magnetic field of an external magnet coupled to the support arm to advance the intracavity device out through an access site and outside the patient. In other variations, a retrieval device (not shown) may be advanced from the body cavity or lumen and through an access site (e.g., trocar or natural orifice) to an exterior of the patient. Once the intracavity device and retrieval device are coupled, the external magnetic positioning device may be decoupled from the intracavity device by, for example, moving the external magnet away from the patient, by reducing a current applied to the external magnet where the external magnet is an electromagnet, or by applying energy to reduce the magnetic field when the external magnet is an electropermanent magnet. The intracavity device may then be advanced out of the body cavity or lumen using the retrieval device. The retrieval device may be the same as a delivery device used to advance the intracavity device into the body cavity or lumen, or a separate device.

It should be appreciated that the operator may input a control signal (e.g., movement signal, magnetic field strength signal) to control the plurality of intracavity devices using an input device as described herein. The operator may be in the same or a different room as a patient, and may be monitored by other users remotely. In some variations, the operator may actuate the intracavity device using the delivery device (e.g., close the jaws of a grasper by actuating the delivery device).

Visualization Device Example

When the intracavity device is a visualization device, the methods may comprise imaging one or more intracavity devices and tissue in a body cavity or lumen for display to an operator. A position and/or magnetic field of an external magnetic positioning device may be modified to move and/or orient the visualization device to provide different fields of view. More particularly, an operator may operate a graphical user interface to control a field of view of an image displayed on an output device. The operator may, for example, modify a location and/or orientation of a visualization device in order to view different tissue and/or intracavity devices.

Grasper Example

When the intracavity device is a grasper, the method may comprise releasably connecting a grasper (such as one of the graspers described here) to tissue. The delivery device may be used to insert the grasper into a body cavity or lumen through a port or other access site. To connect the grasper to the tissue, the grasper may be releasably coupled with a delivery device, wherein the delivery device is configured to actuate the grasper. The delivery device may actuate the grasper to releasably connect the grasper to tissue, and may eject or otherwise decouple from the grasper after the grasper is connected to tissue. When the grasper is decoupled from the delivery device, the grasper may be attracted by a magnetic force generated by a magnet of an external magnetic positioning device. The attraction between the grasper and the external magnet may allow the grasper to move or otherwise hold tissue without the need to have a shaft or other portion of a device positioned in a port or other access site. This may reduce the number of access sites required to provide remote suspension of tissue, which may allow for faster and more reliable surgical procedures.

Once the grasper is connected to the tissue, a position and/or magnetic field of an external magnetic positioning device may be modified to move and/or orient the grasper and the grasped tissue to provide, for example, traction to the tissue. In some variations, an operator may provide input to a graphical user interface, as discussed herein, to control the positioning of the grasper using the external magnetic positioning device. When the grasper in the body cavity or lumen is imaged by a visualization device and displayed on a graphical user interface, the operator may select the imaged grasper for control. Operator input to control a position and/or orientation of the grasper may result in control signals output to the external magnetic positioning device. For example, the operator may "drag and drop" the imaged grasper to a location closer towards a patient cavity wall. This operator input control signal (e.g., movement control signals) may correspond to an output of an external magnetic positioning device control signal to increase the attraction of the grasper to the external magnetic field (e.g., by increasing the current to an external electromagnet and/or bringing the external magnet closer to the patient body surface). In some instances, the delivery device (or another device, such as a grasping device) may be used to disconnect the grasper from tissue. The grasper may then be repositioned and reattached to tissue (either the same tissue or a different tissue), or may be removed from the body.

Retractor Device Example

When the intracavity device is a retractor, the method may comprise forming a sling using a retractor (such as one of the retractors described here) to retract tissue. The retractor may be releasably coupled with a delivery device and advanced into a patient body cavity through an access site. The retractor may be in a low-profile (e.g., substantially linear) configuration when coupled to the delivery device. A portion of the retractor may be positioned underneath a portion of tissue, such that at least a portion of the tissue may be suspended by the retractor and then moved towards the patient body cavity wall. In some variations, the retractor may be configured to transition between a substantially linear configuration and the curvilinear configuration (e.g., by using an external magnetic field). The curvilinear configuration may support and suspend at least a portion of tissue (e.g., an internal organ) from the patient wall in response to a magnetic field.

In some variations, an operator may provide input to a graphical user interface, as discussed herein, to control the positioning of the retractor using the external magnetic positioning device. When the retractor in the body cavity is imaged by a visualization device and displayed on a graphical user interface, the operator may select the terminal ends of the imaged retractor for control. Operator input to move the terminal ends of the retractor towards the patient cavity wall may result in control signals output to the external magnetic positioning device. For example, the operator may "drag and drop" the imaged retractor terminal ends to a location closer towards the patient cavity wall. This operator input control signal (e.g., movement control signals) may correspond to an output of an external magnetic positioning device control signal to increase the attraction of the retractor to the external magnetic field (e.g., by increasing the current to an external electromagnet and/or bringing the external magnet closer to the patient body surface) to thereby retract tissue.

Although the foregoing variations have, for the purposes of clarity and understanding, been described in some detail by illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described herein, the steps of the methods may not be performed sequentially. Some steps are optional such that every step of the methods may not be performed.

The invention claimed is:

1. A system for manipulating tissue, comprising:
an intracavity device configured to be advanced through an access site into a body cavity of a patient;
an external magnetic positioning device configured to magnetically couple to the intracavity device through a body cavity wall, the external magnetic positioning device comprising a force sensor configured to measure a contact force of the external magnetic positioning device on an external surface of the body cavity wall;
a controller comprising a processor and memory, the controller configured to receive the contact force from the force sensor to control a position of the external magnetic positioning device; and
a display coupled to the controller, wherein the controller is configured to generate a graphical user interface on the display, the display comprising a touch surface configured to receive a control signal via operator contact to control a function of the intracavity device within the body cavity.

2. The system of claim 1, wherein the controller is configured to control the external magnetic positioning device to magnetically hold the intracavity device in the body cavity.

3. The system of claim 1, wherein the controller is configured to move the external magnetic positioning device coupled to the intracavity device in response to the graphical user interface receiving operator input to control the intracavity device.

4. The system of claim 1, wherein the intracavity device is configured to generate an image of a portion of the body cavity, and wherein the graphical user interface is configured to generate an intracavity device control button using the image of the portion of the body cavity generated by the intracavity device.

5. The system of claim 4, wherein the image is a real-time image.

6. The system of claim 1, further comprising a second intracavity device, wherein the graphical user interface is configured to simultaneously control both of the intracavity devices.

7. The system of claim 1, wherein the external magnetic positioning device comprises a support arm and a magnet coupled thereto, wherein the controller is configured to generate the graphical user interface configured to receive a location of the magnet, and the support arm configured to moveably suspend the magnet externally of the patient and to move the magnet to the received location.

8. The system of claim 1, wherein the external magnetic positioning device comprises a support arm and a magnet coupled thereto, wherein the support arm is configured to be temporarily locked to fix a position of the magnet.

9. The system of claim 1, wherein the external magnetic positioning device comprises a support arm and a magnet coupled thereto, wherein the support arm is configured to be moved manually by the operator.

10. The system of claim 9, wherein the support arm comprises a handle configured to be moved manually by the operator.

11. The system of claim 1, wherein the external magnetic positioning device comprises a support arm and a magnet coupled thereto, wherein the support arm is configured to move using both the controller and manual movement of the support arm by the operator.

12. The system of claim 1, wherein the external magnetic positioning device comprises a support arm and a magnet coupled thereto, wherein the support arm is an articulated robotic arm.

13. The system of claim 1, wherein the operator contact corresponds to a surgeon contact.

14. The system of claim 1, wherein the operator contact is remote from the patient.

15. The system of claim 1, wherein the external magnetic positioning device comprises a wireless transmitter and the force sensor transmits the contact force to the controller via the wireless transmitter.

16. The system of claim 1, wherein the intracavity device comprises one or both of a visualization device and a tissue manipulation device.

17. The system of claim 1, wherein the external magnetic positioning device further comprises one or more of a proximity sensor and a magnetic field sensor.

18. The system of claim 1 further comprising a delivery device configured to releasably engage the intracavity device and actuate the intracavity device.

* * * * *